United States Patent
Becker et al.

(10) Patent No.: US 6,441,134 B1
(45) Date of Patent: Aug. 27, 2002

(54) **ISOLATED *CANDIDA ALBICANS* OLIGOPEPTIDE TRANSPORTER GENE**

(75) Inventors: Jeffrey M. Becker, Knoxville, TN (US); Mark A. Lubkowitz, Berkeley, CA (US)

(73) Assignee: The University of Tennessee Research Corporation, TN (US)

( * ) Notice: Subject to any disclaimer, the term of this patent is extended or adjusted under 35 U.S.C. 154(b) by 0 days.

(21) Appl. No.: 09/165,396

(22) Filed: Oct. 2, 1998

Related U.S. Application Data

(63) Continuation of application No. PCT/US98/02332, filed on Feb. 6, 1998.
(60) Provisional application No. 60/037,859, filed on Feb. 7, 1997.

(51) Int. Cl.[7] ................................................. C07K 1/00
(52) U.S. Cl. ...................... 530/350; 530/370; 530/371; 530/350; 536/23.6; 536/23.2; 536/23.4; 435/240.4; 435/320.1; 435/254.2; 435/252.3; 435/325; 435/183; 435/7.1; 435/7.2; 436/501; 436/518
(58) Field of Search ...................... 800/205; 435/240.4, 435/320.1, 252.3, 325, 183, 7.1, 7.2, 254.2; 530/370, 371, 350; 536/23.2, 23.4, 23.6; 436/501, 518

(56) References Cited

PUBLICATIONS

Basrai et al., Microbiology, vol. 141, pp. 1147–1156, 1995.*
Alingment.*
Fei et al., Expression Cloning of an Mammalian Proton–Coupled Oligopeptide Transporter. Nature, Apr. 7, 1994, vol. 368, pp. 563–566, especially Figure 1 on p. 563.
Fling et al., Analysis of a Candida Albicans Gene that Encodes a Novel Mechanism for Resistance to Benomyl and Methotrexate. Molecular & General Genetics. 1991, vol. 227, pp. 318–329, especially Figure 3 on pp. 322 and 323.

* cited by examiner

*Primary Examiner*—Karen Cochrane Carlson
*Assistant Examiner*—Hope A. Robinson
(74) *Attorney, Agent, or Firm*—Schnader Harrison Segal & Lewis LLP

(57) ABSTRACT

A *Candida albicans* oligopeptide transport gene, OPT1, was cloned from a *C. albicans* genomic library through heterologous expression in the *Saccharomyces cerevisiae* di-/tripeptide transport mutant PB1X-9B. When transformed with a plasmid harboring OPT1, *S. cerevisiae* PB1X-9B, which did not express tetra-/pentapeptide transport activity under the conditions used, was conferred with an oligopeptide transport phenotype as indicated by growth on the tetrapeptide Lysyl-Leucyl-Leucyl-Glycine, sensitivivity to toxic tetra- and pentapeptides, and an increase in the initial uptake rate of the radiolabeled tetrapeptide Lysyl-Leucyl-Glycyl-[$^3$H]Leucine. The entire 3.8 kb fragment containing the oligopeptide transport activity was sequenced and an open reading frame of 2349 nucleotides containing a 58 nucleotide intron was identified. The deduced protein product of 783 amino acid residues contained twelve hydrophobic regions suggestive of a membrane transport protein. The oligopeptide transporter facilitates targeting of antifungal, especially anticandidal drugs.

10 Claims, 11 Drawing Sheets

FIG. 3

| FIG. 3a |
|---------|
| FIG. 3b |
| FIG. 3c |

```
Opt1         ..........  ..........  ..........  ..........  ..........  ..........  MDki RaViSggEkp   14
Isp4         ..........  ..........  ..........  ..........  ..........  ..........  .mIgSInEsp         9
SCYJL212C    ..........  ..........  ..........  ..........  ..........  msti yresdsLEse psptpttipi   24
YSCP9677     msetvkakvi  idekvstkgt  vdyaegaeys  erlsnhssdf  sqwytdeqil  hfmkklgyen Rtlydlp Edv       70
Consensus    ---------   ---------   ---------   ---------   ---------   --------   R---SI-E---

Opt1         pVDtDNDhnt  dFEadrKmpd  lDIVVSKsqe  .FDPvtshlv  ndimEDEyaa  V....hvED.                    68
Isp4         ieEhmNDsps  TkEKadsVDI  sDyIVShsDD  sLskDikKdt  KsfIDvEhgE  IstvdEFEE.                    68
SCYJL212C    qInMEeEkkd  aFVknideDV  nnltattdEE  drDPEsqKfd  rhsiqEEgLv  wKgdptYlp.                    83
YSCP9677     ayiLkkmpel  TLEdsfKIIk  dsIIyfKdDe  niphDqyeew  KrLvDIEdLD  sKegiDeyDs fdirafasai        140
Consensus    -----ND---  TFEK--K-D-  -DIIVSK-DE  --DPD--K--  K---D-E-L-  -K------ED- Opt1         ..DSPYPEVR  AAVPstDDPT  lPqNTiRAWv  iGLILttVGc  GmNMLFSFhs  PsfaitTFVt siLAWPIGnf        136
Isp4         ..DSPYPEVR  AAVPPtDDPs  mPcNTiRmWt  iGLIYStVGA  aVNMFFSLRn  PtvtlsvLIs eILAYPalqI        136
SCYJL212C    ..nSPYPEVR  sAVsieDDPT  irlNhwRtWF  lttVFvvVFA  GVNqFFSLRy  PSleiNFLVa QvvcYPIGrI        151
YSCP9677     kfhSPYqEVR  AVVdPeDDPT  iPveTfRAYF  laiIWSvIGs  GfNeFFShRv  vSisINIpIi QmFlYicGka       210
Consensus    --DSPYPEVR  AAVPP-DDPT  -P-NT-RAWF  -GLI-S-VGA  GVNMFFSLR-  PS----NTL-- Q-LAYPIG-I Opt1         WAwIvPDWKI  .....FgasLN PG. PFnVKEH  tiITIManVS  FgtGAAYATd  IILAQnMFYK SnFGWGYnLL        201
Isp4         WdLIFPDRef  rIgrLKFnFk  PG. PFnvKEH  AIIvVMssvS  F..GnAYsTd  IiLAQrvhYK qrFGFGYeic        203
SCYJL212C    IAL.IPDWKc  skvpF.FdLN  PG. PFtkKEH  AvVTI..AVa  LtsstaYAmy  IlnAQgsFYn mKLnvGYQFL        216
YSCP9677     WAKtiPcWtI  tIrgrKYgiN  idkPWtqKEq  mfsTILyAIc  ..qGaFYthy  niLtQkLFYh SaFsFGYQFL        278
Consensus    WALI-PDWKI  -I--FKF-LN  PG-PF-VKEH  A-ITIM-AVS  F--GAAYAT-  I-LAQ--FYK S-FGFGYQFL
```

FIG. 4

| FIG. 4a |
|---|
| FIG. 4b |
| FIG. 4c |

FIG. 4a

```
Opt1       LIWSTQcIGF aFgGvMRRFV VdspgAiWPI NLVTaTFLtn MHinE..Nht ANGWkiSRLa FFvIVFVASF 269
Isp4       LtIaTQLIGY GLAGIsRRLI VrPASmIWPv NLVqcTLiKt LHrKDIrNaV ANGWriSpFR FFLyVFIASF 273
SCYJL212C  LVwtsQMIGY GaAGItRRWV VnPASsiWPq tLIsVsLFds LHsrkvektV ANGWtmpRYR FFLIVLIgSF 286
YSCP9677   LsISvQFIGF GFAGiLRkFV VyParAIWPt vMpTIainKa LIgKE..... khesgmSRYk FFFItFfimF 343
Consensus  L--STQ-IG- GFAG--RRFV V-PASA-WP- NLVT-TL-K- LH-KE--N-V ANGW--SRYR FFLIVFIASF Opt1       VWyWFPGYIF QALSYFsWIT W..IKPNNVI INQVFGsSsG LGmiPnnIaL DWNQIa.gYI GSPLIpPasV 336
Isp4       IWnWSPsYIF QALSIFaWVT W..IRPTspt VNQIFGeStG isILP..mTF DWNQIS.AYI ISPLmaPada 338
SCYJL212C  IWyWVPGFIF tgLSYFNvIl WgskTrhNFi aNtIFGtqsG LGaLP..ITF DYTQVSqAms GSvFatPfYV 354
YSCP9677   IYnWFPtYIi niLntFNwmT W..IKPsNIn IanItGgvtG LGInPis.sF DWNvIS...f nSPLVyPfWs 407
Consensus  -STTY--SYG LSFA-I-AVI TH-ILYHGKD --A--KD--- --------- --------R ----PDIH-R Opt1       iatIFgsIVL iFWIVVPAih YsNTWYsQYL PISStgsFDr fqqtYNVsKI iDhKtISFne aeYkkYSPIF 406
Isp4       ImnILLgVIL FFWIVtPAIn FtNTWYgdYL PISSsgiiDh fgNSYNVTrI Lt.KDatFdL DaYqnYSPIF 407
SCYJL212C  santYasVLi FFvIVIPcIY FtNTWYakYM PViSgstYDN tqNkYNVTKI Ln.eDySinL EKYkeYSPVF 423
YSCP9677   yItqYLgciL aaIVI.AvY YsNymscQYL PiftnsIYtN tghSFkVTeV LD.sDnkLdv kKYqsYSPpY 475
Consensus  ---IYL-VIL FFWIV-PA-Y --NTWY-QYL PISS----YDN --NSYNVTKI LD-KD-SF-L -KY--YSP-F Opt1       LSTTFaiSYG LSFAsIIAtI THtIcFHGrD IiAsLKa... .......... k..EkPDVHnR 452
Isp4       MSTTYaIaFG LSFAsItsVI fHvILYHGKE iydrLrD... .......... p..paPDIHek 453
SCYJL212C  vpfsYIiSYa LnFAaViAVF vHcILTHGKD ivAkFKD... .......... R knggtDIHmR 471
YSCP9677   ySagnIvSYG aFicaypImI Twsfivhskl IfnaFKDwal nIwamrkIks wvtmfksdyR aIDdyDdphs 545
Consensus  -STTY--SYG LSFA-I-AVI TH-ILYHGKD --A--KD--- ---------- ---------R ----PDIH-R Opt1       LM.KaYKpVP EWWYLvVFIV FFGMsIATVr aWPTEmPVWG LVFaIIiaiI FLIPVaIiyA KTNIavGLNV 521
Isp4       LM.KaYdEVP FYWYLsVFIa FFGMmmgTIY gWkTETPwwv iIVgvIFSaV WFIPIGIvQA iTNIqIGLNV 522
SCYJL212C  iysKnYKDcP DWWYLIIqiV miGLGfvaVC cFdTkFPaWa FVIAiIiSLV nFIPqGIIeA mTNqhvGLNI 541
YSCP9677   namKnYKEVP DWWYFaILig sLvgIAvVe hYPTnTPVWG LFVcIgFnFV FLIPttIIQA tTgysFGLNI 615
Consensus  LM-K-YKSVP DWWYL-VF-V FFGMGIATV- -WPTETPVWG LVVA-I-S-V F-IP-GI-QA -TNI--GLNV FIG. 4b
```

```
Opt1        vTEFIVGYvL gGRPLcmmlF TKFGYItnnQ avtFVqDMKL gHYMKIdPRt LFWaQfaATI wgsLVqIaVL 591
Isp4        fTEFIVGYMy PGRPLAMMiF KTvGYItMtQ gLaFaaDLKF gHYMKlPPRi MFYtQmIATI wScFVqIGVL 592
SCYJL212C   iTELlcGYML PlRPMAnLlF KlYGFIvMrQ gLNLsrDLKL amYMKVsPRl iFavQiyATI iSgMVnVGVq 611
YSCP9677    liEMvmGYaL PGnPiAiMiL KaFGYniDGq adNYVsnLKi aHYcKIPPma LFRgQcVivf iqiFVnlGVL 685
Consensus   -TEFIVGYML PGRPLAMM-F KTFGYI-M-Q -LNFV-DLKL -HYMKIPPR- LF--Q--ATI -S-FV-IGVL Opt1        EWAyGaIDNL CaAdQkNhYT CPNgkvFFNA SIIWGVIGPq RqFShGqIYy GLLFFFiIGA vtPVinWlIl 661
Isp4        DWALGNIDNv CqADQPdnYT CPNatvFFNs SVIWGVIGPK RMFSgkntYt GLqYFWLaGv LgtILfWAlW 662
SCYJL212C   EWmMhNIDgL CTtDQPNgFT CaNgrtvFNA SIIWsl..PK yLFSsGrIYn pLMWFFLIGl LfPlavYAVq 679
YSCP9677    nWqisNIkdF CTphQnakFT CPdavtYYNA SVVWGaIGPK RiFny..IYp iFkWcWLIGA cigIF.FgVW 752
Consensus   EWA-GNIDNL CTADQPN--T CPN---FFNA S-IWGVIGPK R-FS-G-IY- GL-WF-LIGA L-PI--WAVW Opt1        KKWPn.spvK yLHwPvFFsG TGYIPPaTPY NYtsYcA... VgLFFgWWiK KkWfhWWsKY NYsLSAGLDi 727
Isp4        KKWPq.KWWg qLngPliFgG TGYIPPaTPv NYLaWsg... IgLFFNYYlK KiFadWWqKY NFtLSA.LDT 727
SCYJL212C   wKFPkfKFak hiHtPvFFtG pGnIPPsTPY NYslFfA... msFcLN.lir KrWraWFnKY NFVMgAGvEa 745
YSCP9677    KrWg..KFYp ryfdPmLFvG .GmlnmspPy NlMyYtsgmi VsYisqYYmK rhhLnlWeKY NYVLSAGFsT 819
Consensus   KKWP--KF-K -LH-P-FF-G TGYIPP-TPY NY--Y-A--- V-LFFNYY-K K-W--WW-KY N-VLSAGLDT Opt1        GLAwcslIIF LClsltnTdF PSWWGNDVin tTLDtqvvtn IRhiLKEGEa FGpssW...            783
Isp4        GtqLSVlIlF FClQlPmvnF PdWWGNDgaF nTLDa.tgaa VRklvnEsar .........            776
SCYJL212C   GvAiSVVIIF LCvQyPggkL .SWWGNnVwk rTyDndykkF y..TLKkGEt FGYdkWw..            799
YSCP9677    GLvLSaIIIF FavQykdTaF .nWWGNtVpY agaDgvgypL kniTdtangy FGYapghyp            877
Consensus    GLALSVIIIF -C-Q-P-T-F PSWWGNDV-- -TLD------ -R-TLKEGE- FGY--W---
```

ISOLATED *CANDIDA ALBICANS* OLIGOPEPTIDE TRANSPORTER GENE

RELATED CASES

This application is a continuation of PCT/US98/02332 filed Feb 6, 1998 which claims the benefit of provisional patent application Ser. No. 60/037,859, filed on Feb. 7, 1997, entitled An Oligopeptide Transport Gene from *Candida albicans*, which is incorporated herein it is entirety by reference.

FIELD OF THE INVENTION

The invention relates to novel nucleic acid sequences encoding peptide transporters, to novel polypeptides and drug delivery systems.

BACKGROUND OF THE INVENTION

Peptide transport, a phenomenon defined as the translocation of peptides across the plasma membrane in an energy-dependent manner, has been well documented in bacteria, plants, fungi, and mammals (for reviews see Becker & Naider, 1995; Payne and Smith, 1994). Upon internalization, peptides are quickly hydrolyzed into their amino acid components to serve as sources of amino acids or nitrogen. In addition to acquiring nutrients from the environment, peptide transport has been shown to play a role in recycling cell wall peptides and in transducing signals for group behaviors such as sporulation and competency in *B. subtilis* and chemotaxis in *E. coli*. Recently it has been proposed that in *Salmonella typhimurium* peptide transporters aid the bacteria in evading the host immune response by transporting membrane disrupting peptides away from the plasma membrane (Parra-Lopez et al., 1993). Similarly, in *Streptococcus pneumoniae* the peptide transporters encoded by plpA and the amiA loci play a role in virulence by modulating adherence to epithelial and endothelial cells (Cundel et al., 1995).

A family of di-/tripeptide transporters named the PTR (Peptide TRansport) Family has recently been identified. This family is characterized by several conserved motifs, has twelve putative transmembrane domains, and is driven by the proton motive force. Members of the PTR family have been identified in a broad variety of eukaryotes and one prokaryote as well (Steiner et al, 1995). Well characterized members of the PTR family are the di- and tripeptide transporters from *S. cerevisiae* (ScPTR2, Perry et al., 1994) and from *C. albicans* (CaPTR2, Basrai et al., 1995). Both CaPTR2 and ScPTR2 have been shown to be regulated by nitrogen source and inducible by micromolar amounts of amino acids; their encoded proteins have broad substrate specificities with a preference for peptides containing hydrophobic residues (Basrai et al., 1992; Island et al., 1987). Prior to the establishment of the PTR family, all peptide transporters cloned were from prokaryotes and were members of the ATP Binding Cassette (ABC) Superfamily (Higgins, 1992). Recently, transporters from the PTR family have been identified in the prokaryote *Lactococcus lactis* (Hagting et al., 1995). However, in eukaryotes all peptide transporters thus far identified are members of the PTR family.

In addition to the di-/tripeptide transporter (CaPTR2) in *C. albicans*, three observations indicated the existence of another distinct peptide transport system. The first observation was that mutants resistant to the toxic peptide analogs bacilysin, polyoxin, and nikkomycin Z (all demonstrated substrates of the di-/tripeptide transport system) were able to transport tetra- and pentapeptides at wild type levels, and, conversely, mutants resistant to various toxic tetrapeptides were able to transport dipeptides at wildtype levels (Payne and Shallow, 1985; Milewski et al., 1988; McCarthy et al., 1985). Secondly, peptide uptake experiments with radiolabeled compounds and chromophoric substrates demonstrated that dipeptides did not compete with tetra- and pentapeptides for entry into the cell, and vice versa tetra- and pentapeptides did not compete with labeled dipeptides (Milewski et al., 1988; McCarthy et al., 1985; Yadan et al., 1984).. Thirdly, sensitivity to toxic di- and tripeptides was influenced by nitrogen source and micromolar amounts of amino acids while sensitivity to toxic tetra- and pentapeptides was not regulated by similar means (Basrai et al., 1992). The invention described herein relates to the cloning of a novel oligopeptide transporter from *C. albicans* that does not code for an ABC- or PTR-type transporter.

SUMMARY OF THE INVENTION

The invention relates to a new transporter system: a system to transport oligopeptides as opposed to lower peptides. The invention relates to an oligopeptide transporter competent to transport higher oligopeptides, especially tetra- and pentapeptides. The expression of transport activity is evidenced in a heterologous host suggesting that the transporter is an integral membrane transporter. The ability to transport peptides of a size larger than di/tripeptides is highly significant in that it will permit the delivery of greater variety of biological molecules in molecular structure and size into the selected target.

Furthermore, there is provided a novel peptide transport gene from *Candida albicans* through heterologous expression in *Saccharomyces cerevisiae*, which encodes an oligopeptide transporter OPT, which is different from the previously identified family of di-/tripeptide transporters named the PTR (Peptide Transport) family. The gene encoding OPT1 appears to constitute the first identified member of a new family of oligopeptide transporters.

The gene sequence revealed the presence of two ORFs separated by a type II intron, and encoding a hydropholic protein of 783 amino acids with an apparent molecular mass of 88 kDa and a pI of 7.1. The size and hydrophobic nature of the predicted protein of OPT1 suggest a membrane/bound protein with at least 12 putative transmembrane domains of 20–24 amino and residues. Findings made in connection with invention indicate that OPT1 is not a member of the PTR or ABC families of membrane transporters.

Peptide utilization mediated by OPT1 showed its ability to mediate the uptake of Lys-Leu-Gly (KLG), Lys-Leu-Leu-Gly (KLLG) SEQ ID NO:6, Lys-Leu-Gly-Leu (KLGL) SEQ ID NO:7 and Lys-Leu-Leu-Leu-Gly (KLLLG) SEQ ID NO:8.

Various eukaryotic transformants of the yeasts are made available by the invention.

The invention provides peptide transporters as a means to facilitate the uptake of otherwise nonpermeating biologically active molecules of medical significance, such as antifingal compounds.

Heretofore it was known that *C. albicans* can transport and utilize small peptides. The invention allows using *C. albicans* with the novel oligopeptide transporter for the uptake of peptide-drug adducts. In the search for effective antimicrobial drugs, substances are often found that display toxicity towards intracellular targets when tested in cell-free systems, but are inactive with intact organisms. Frequently this occurs because the potentially toxic agent is impermeable. The invention provides a drug delivery system whereby a toxic moiety is linked or otherwise carried by a molecule which will be taken up and actively transported through a specific permease for delivery to the target. But for the membrane transporter system described herein, such drug delivery system are known. For instance, the uptake by dipeptides containing $N^3$-(4-methoxyfamaroyl)-L-2,3-diamino-propanoic acid (FMDP) has been extensively studied. Literature references dealing with such drug delivery designs are incorporated herein by reference. For instance, it is known that N-acylation can stabilize the carrier toxic agent conjugate to amino peptidase activity. See Peptide Base Drug Design, Becker and Naider cited herein.

Infections attributable to *C. albicans* are wide spread. The oligopeptide transport system of the invention is useful to deliver anticandidal drugs carried (conjugated or linked or associated) and taken up by the peptide, delivered to the transporter which will deliver it through the membrane to the target.

The oligopeptide transporter of the invention will promote the more effective delivery of anti candidal drugs into organisms infected by *C. albicans*. Such drugs can be molecules like toxic peptides carried, if necessary by a carrier, or molecules that mimic or are similar in character to the peptides, like peptido-mimetics. The invention also provides for the delivery of the OPT1 gene into a mammalian target call where it will express the oligopeptide transporter, thereby facilitates the targeting of the desired drug.

The ability to use the transport system encoded by the OPT gene will allow delivery of toxic agents specifically into cells or organisms expressing this gene. Thus, if pathogenic fungi express such a gene in an infected human host that is not capable of expressing this gene, then antifungal agents can be designed to kill the invading pathogen without having any adverse effects on the human host. Such non-toxic antifungal agents are the major goal of all pharmaceutical companies with antifungal drug programs. Currently, extensive research is carried out throughout the world in the search for antifungal drugs.

The OPT gene of *C. albicans* opens the way for gene discovery of a family of plant oligopeptide transport genes. Genes in the family represented by the OPT gene of *C. albicans* have been found to date only in other fungi, and some potential homologous genes have been noted in the plant EST database. Using fungi as the heterologous hosts for testing oligopeptide transport ability, full-length plant genes should be uncovered and characterized by techniques used in this invention to clone di-/tripeptide plant transporters. Thus, oligopeptides might be useful agents as herbicides or growth stimulators depending on the chemical constituents of a modified oligopeptide. Delivery of such oligopeptide-based analogs to plant cells via the oligopeptide transport system would allow specificity in targeting. Also, uptake into the plant cell would occur in large quantities due to the ability to transport systems to concentrate substrates intracellularly to high levels.

Other embodiments will become apparent from the description that follows.

DESCRIPTION OF THE DRAWINGS

FIG. 3 is a nucleotide SEQ ID NO:1 and predicted amino acid sequences SEQ ID NO:2 of OPT1. The predicted amino acids are italicized and numbered to the left of the figure while nucleotides are numbered to the right. The 5' and 3' splice sites as well as the conserved branch point of the intron are boxed. The codon CUG (CTG in the DNA) encodes serine not leucine in *C. albicans* (Omaha et al., 1993).

FIG. 4 is a comparison of oligopeptide transporters. The proteins Opt1, SEQ ID NO:2 lsp4, SEQ ID NO:3 SCYJL212C SEQ ID NO:4 and YSCP9677 SEQ ID NO:5 were aligned using the program PileUp. Conserved residues are in upper case and denoted as the consensus, while nonconserved residues are in lower case. The amino acids in each respective protein are numbered to the right.

The following experimental results and examples are not intended to be limiting but rather illustrative of the invention.

DESCRIPTION OF RESULTS OF THE PREFERRED EMBODIMENT

Cloning of an Oligopeptide Transporter

Recently, the cloning of di- and tripeptide transporters of *Candida albicans* (CaPTR2) (BasraiÊet al., 1995) and *Arabidopsis thaliana* ( AtPTR2-A and AtPYR2-B) (Steiner et al., 1994; Song, et al., 1996) (U.S. Pat. No. 5,689,039) through heterologous expression in *Saccharomyces cerevisiae* has been reported. Unlike *C. albicans*, *S. cerevisiae* has been found to transport only a limited number of tetra- and pentapeptides under a limited number of growth conditions (reviewed by Becker and Naider, 1995). Therefore, as initial strategy the *S. cerevisiae* di-/tripeptide transport mutant PB1X-9B was transformed with a high copy number *C. albicans* genomic library and screened for the ability of *S. cerevisiae* to grow on a normally non-utilized tetrapeptide as a sole source of auxotrophic supplements.

A pRS202 based *C. albicans* genomic library was transformed into *S. cerevisiae* PB1X-9B and 32,000 URA3$^+$ transformants were obtained. Transformants were pooled into 6 groups of approximately 5,200 transformants each and subsequently plated onto a medium containing 50 μM Lys-Leu-Leu-Gly (KLLG) SEQ ID NO:6 as the sole source of leucine and lysine as well as ammonium sulfate as a nitrogen source. A double auxotrophic selection was employed to preclude the possibility of cloning the *C.*

*albicans* LEU2 or LYS1 homologs. *S. cerevisiae* PB1X-9B can not utilize the tetrapeptide KLLG as a sole source of lysine or leucine when grown on a medium containing a rich nitrogen source such as ammonium sulfate (unpublished observation). Oligopeptide transport (OPT) positive colonies appeared after 5–7 days of incubation at 30 C.

Curing of the plasmid by growth in nonselective conditions as well as shuttling the plasmid through *E. coli* and back into *S. cerevisiae* PB1X-9B demonstrated that the OPT activity was plasmid borne. Subsequently two different plasmids, denoted pOPT1 and pOPT24 containing inserts of 3.8 and 4.3 kb respectively, were recovered from a representative sample of OPT+ colonies. Initial restriction mapping demonstrated that the smaller of the two plasmids pOPT1 overlapped entirely with the larger plasmid pOPT24. Therefore, the plasmid pOPT1 (FIG. 1) was used in all subsequent experiments.

Southern Blot

Figure 2:
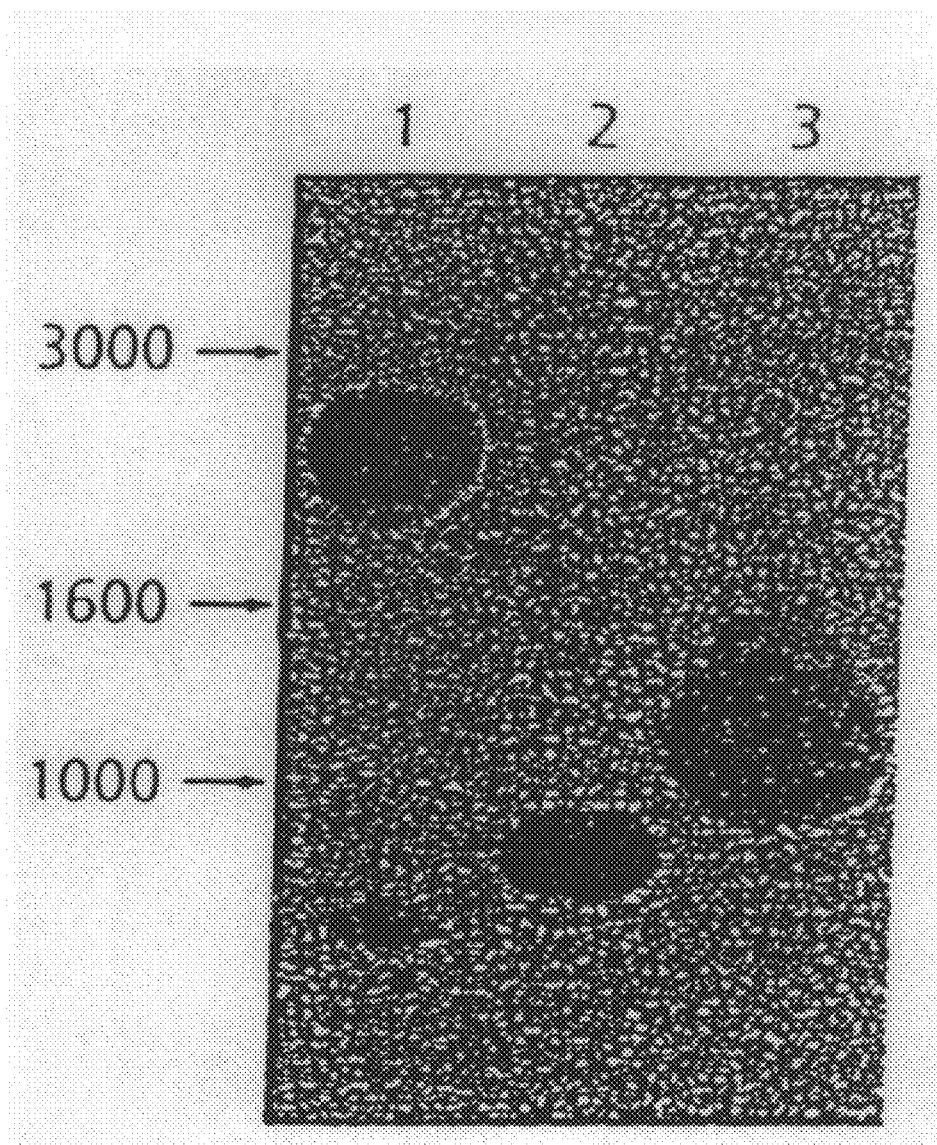
FIG. 2 is a southern blot. Analysis of hybridization of a probe of OPT1 to genomic DNA isolated from *C. albicans* SC5314 was performed as described in Methods. Lanes: 1, Hincll digest; 2, Pvull-BamHl digest; 3, Pvull-Kpnl digest. Size markers are in bp.

Southern blot analysis was done to ensure that OPT1 was derived from *C. albicans* genomic DNA and to determine if there were other homologous genes. Genomic DNA was isolated from *C. albicans* SC5314 and digested with the restriction enzymes HincII, BamHI/PvuII, and PvuII/KpnI. The resulting fragments were separated on a 1% agarose gel and Southern blotting performed as described in materials and methods. The PvuII/KpnI and PvuII/BamHI digests were each predicted to yield one band while the HincII digest was predicted to yield two bands. As seen in FIG. 2, each digest produced their predicted bands; 617 bp and a band of >2700 bp for HincII (Lane 1), 790 bp for PvuII/BamHI (Lane 2), 1163 bp for PvuII/KpnI (Lane 3).

Nucleotide and Deduced Amino Acid Sequence of OPT1

Figures 3, 3A, 3B, 3C:
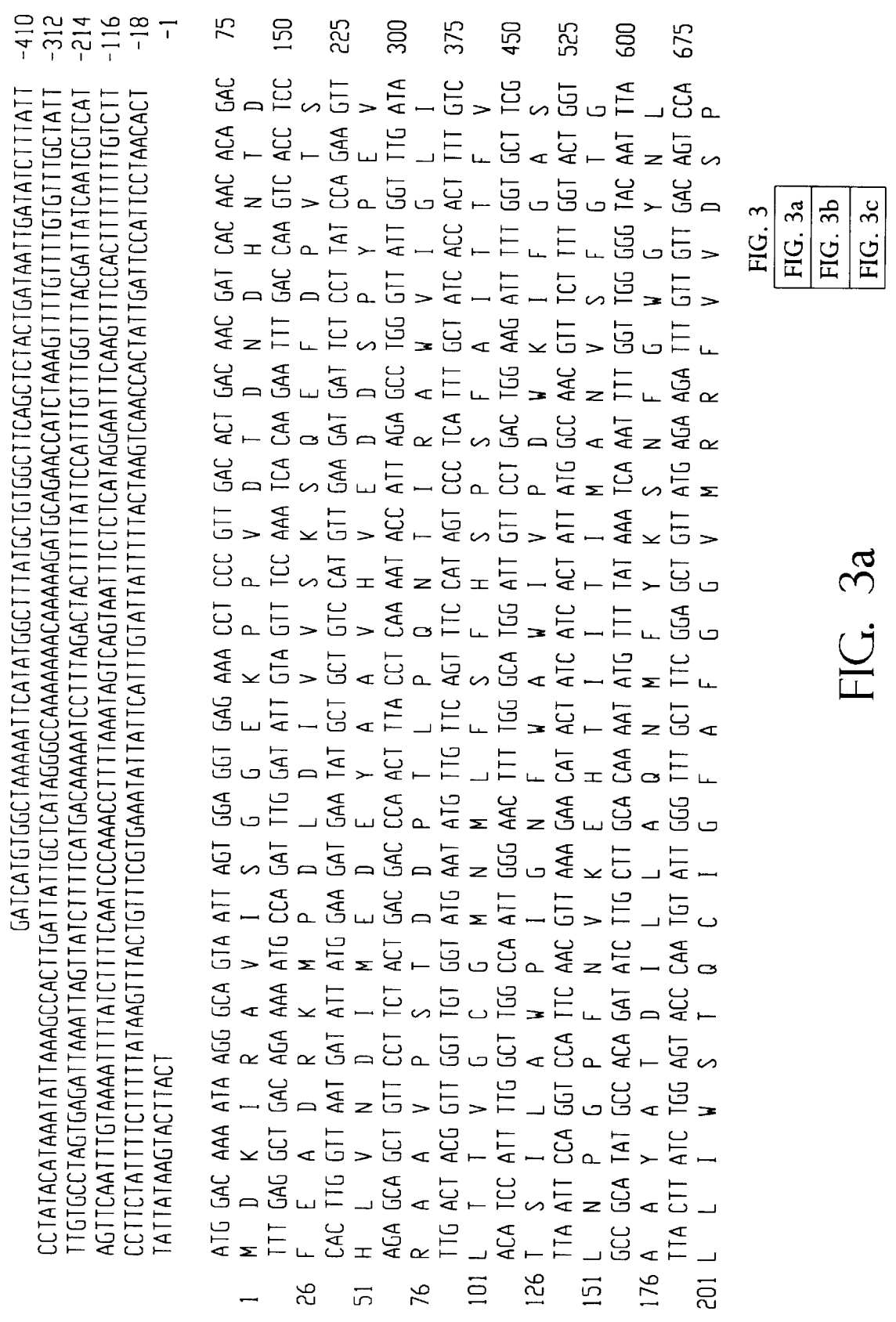
Figure 3B:
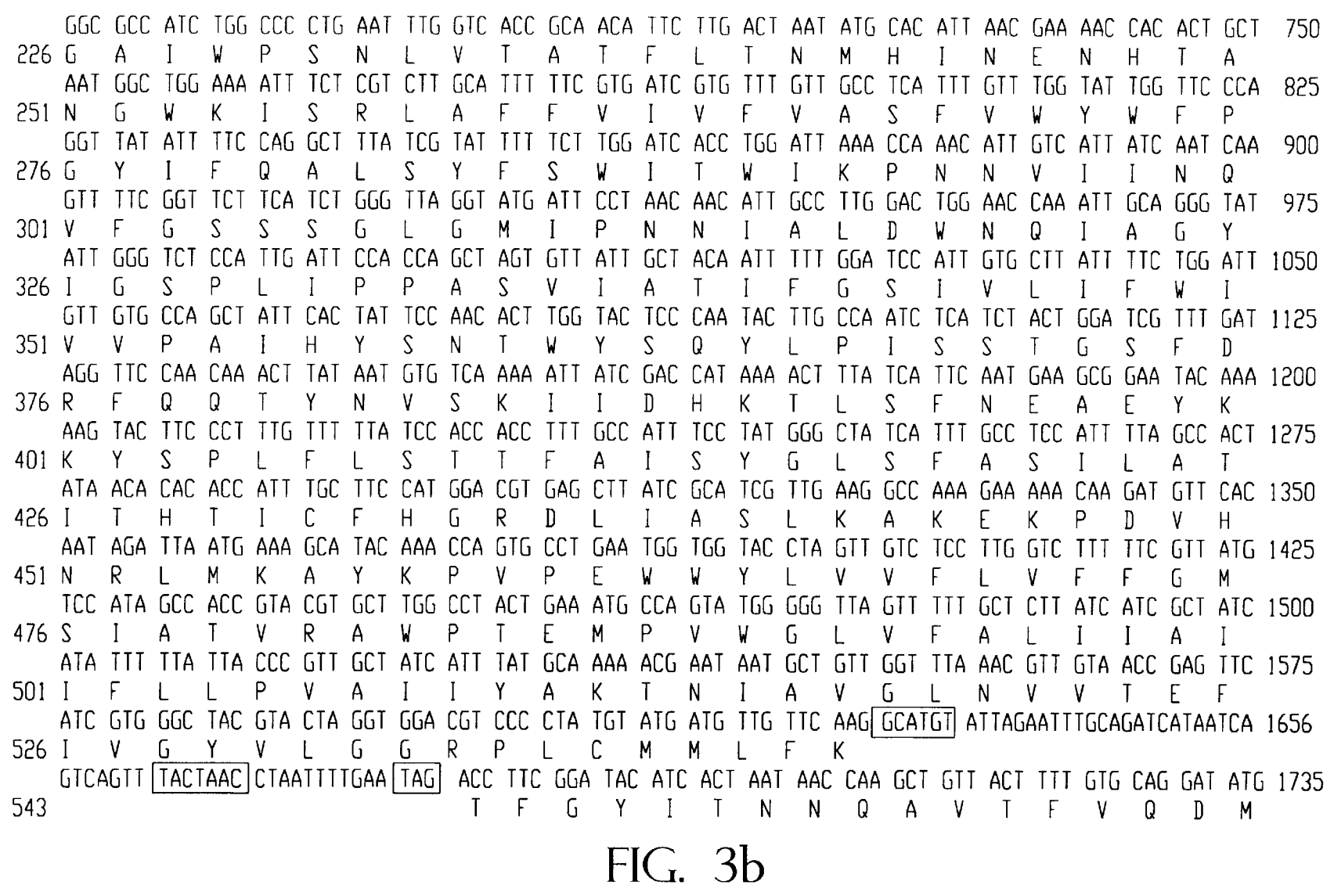
Figure 3C:
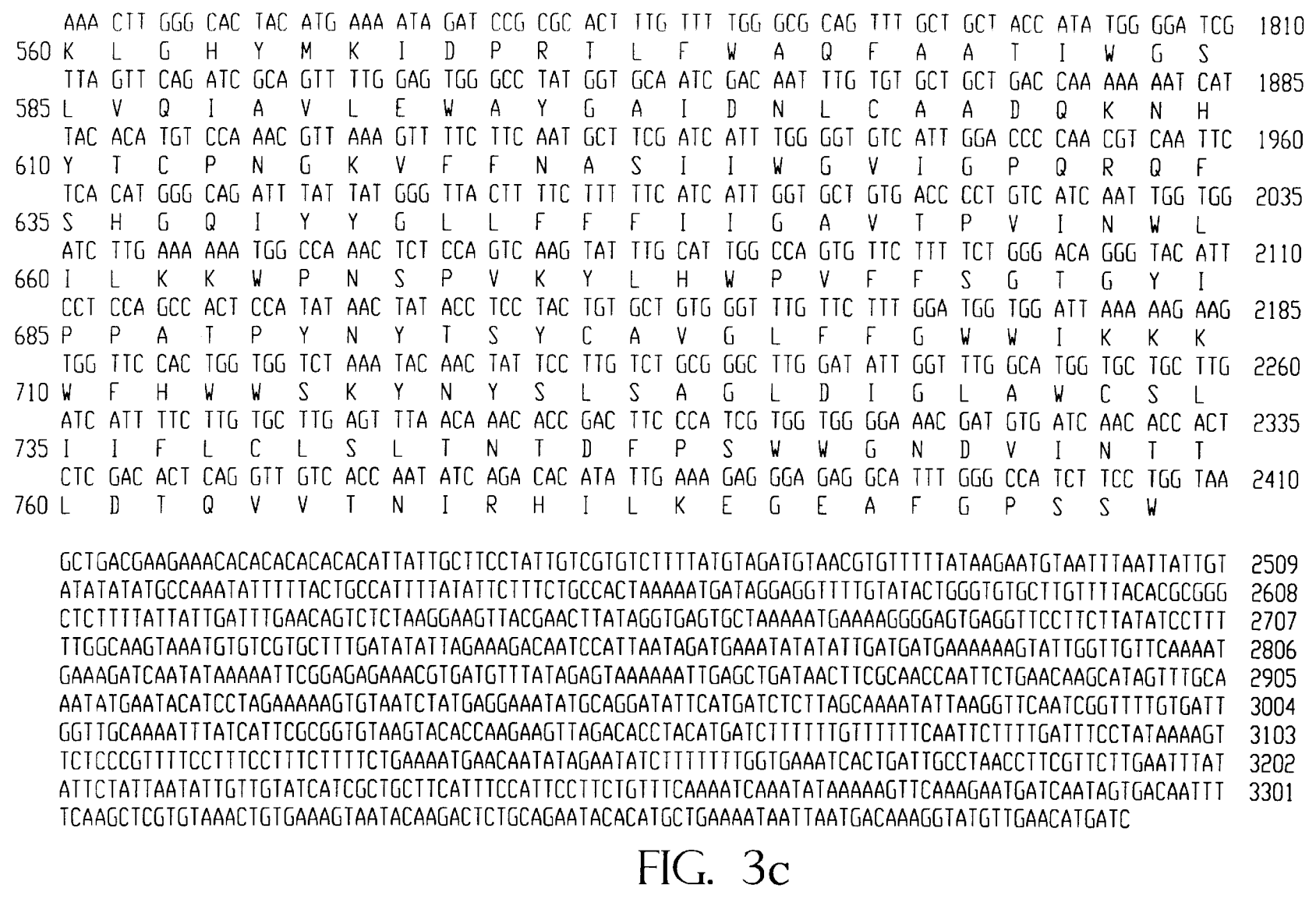

Sequence analysis revealed the presence of two ORFs, separated by a type II intron, and encoding a hydrophobic protein of 783 amino acids with an apparent MW of 88 kD and a pI of 7.1 (FIG. 3). The first ORF contained 1626 nucleotides while the second ORF contained 723 nucleotides excluding the stop codon. The intron separating the two ORFs was 58 nucleotides in length and contained the highly conserved 5Ō splice site (GCATGT), 3Ō splice site (TAG), and branch point (TACTAAC) (Rymond and Rosbash, 1992). The two ORFs and intron constitute the gene OPT1. The size and hydrophobic nature of the predicted protein product of OPT1 are suggestive of a membrane bound protein with at least twelve putative transmembrane domains of 20–24 amino acid residues. These domains form the pathway through which the transported molecular cross the membranes.

Figure 1:
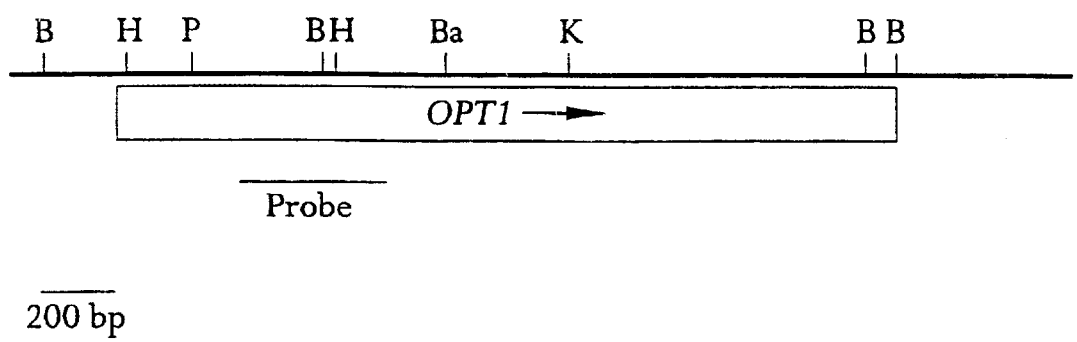
FIG. 1 is a partial restriction map of the 3.8 kb fragment from pOPT1. The location and orientation of the ORF are indicated as well as the location of the probe used in Southern blots. Restriction sites are as follows: B, BstXl; H, Hincll; P, Pvull; Ba, BamHI; K, Kpnl.

Fragments of the nucleotide sequence of FIG. 1, especially from nucleotide 1 to 2410 are within the scope of the invention providing the fragment(s) is functional to encode the oligopeptide transporter described herein or a functional part thereof. Likewise, nucleotide sequences which are adequately homologous to all or a functional part of the sequence of FIG. 1 or the sequence of nucleotide 1 to 2410, are within the scope of the invention.

A search of the database using the BLAST algorithm (Althsul et al., 1990) identified two ORFs from *S. cerevisiae* and one ORF from *S. pombe* as having significant homology. The ORFs SCYJL212C and YSCP9677 from *S. cerevisiae* were identified during the genome sequencing project and were not assigned any function. The remaining ORF, ISP4 from *S. pombe*, was identified as a gene of unknown function that was up-regulated as a result of inducing meiosis through nitrogen starvation (Sato et al., 1994). However, whether this induction was meiosis specific or due simply to nitrogen starvation was not determined.

The predicted protein products of the putative homologs were aligned (FIG. 4) using the PileUp program (Feng and Doolittle, 1987) from the Genetics Computer Group (GCG) software (Devereux et al., 1984) and percent identity and similarity calculated using the GCG program Bestfit. The protein Isp4p from *S. pombe* exhibited the best homology with 48% identity and 70% similarity. The two proteins from *S. cerevisiae* exhibited lower homology with 40% identity and 63% similarity for SCJL212C and 34% identity and 59% similarity for YSCP9677.

The PTR family of peptide transporters is characterized by the signature motif FYXXINXGSLS SEQ ID NO:9 (Steiner, et al., 1995) whereas the ABC transporters are characterized by the ATP binding Walker motifs (Higgins, 1992). The predicted protein product of OPT1 did not contain the PTR signature motif or the ABC Walker motif. Furthermore, a comparison of OPT1 with the PTR di-/tripeptide transporter CaPTR2 using the GCG program Bestfit revealed only 18% identity between the two transporters. These data indicated that OPT1 is not a member of the PTR or ABC families of membrane transporters.

Peptides as Growth Substrates

To determine the size constraints of peptide utilization mediated by pOPT1, the ability of *S. cerevisiae* PB1X-9B (a mutant in the di-/tripeptide transporter) harboring either pRS202 (the parent vector) or pOPT1 (pRS202 containing the 3.8 kb insert with the OPT1 gene) to grow on KL, KLG, KLLG SEQ ID NO:6, and KLLLG SEQ ID NO:8 as a sole source of leucine was tested. Previously it has been shown that di-/tripeptide transport activity in *C. albicans* and *S. cerevisiae* is regulated by nitrogen; rich nitrogen sources such as ammnonium sulfate repress, while poor nitrogen sources such as proline derepress transport. Therefore simultaneous effect of nitrogen source on oligopeptide transport activity was determined by supplying either ammnonium sulfate or proline as the nitrogen source. When grown on a medium containing ammnonium sulfate, PB1X-9B(pOPT1) was only able to utilize the peptide KLLG as a source of leucine whereas PB1X-9B(pRS202) did not utilize any of the peptides tested. When grown on a medium containing 0.1% proline, PB1X-9B(pOPT1) was also able to utilize the tetrapeptide KLLG SEQ ID NO:6 as a sole source of leucine, although the growth was much more robust than the growth exhibited on the ammonium sulfate medium. No growth was observed on KL, KLG and KLLLG SEQ ID NO:8 for PB1X-9B(pOPT1) or PB1X-9B(pRS202).

Sensitivity of *S. cerevisiae* Transformants to Toxic Peptides

*S. cerevisiae* PB1X-9B is sensitive to the toxic amino acid ethionine Eth) but is resistant to ethionine containing di-, tri-, tetra-, and pentapeptides. Disk sensitivity assays was utilized to determine if cells transformed with pOPT1 were sensitive to toxic peptides and whether this sensitivity was dependent upon nitrogen source. In those conditions where ammonium sulfate was used as a nitrogen source, no zone of growth inhibition was seen for the transformed strain in the presence of AEth, LEth, or KLEth, whereas a 33 mm zone of inhibition was seen, for ethionine alone (Table 1). A small and diffuse zone of growth inhibition (about 11–15 mm) was seen for KLLEth SEQ ID NO:12, KLAEth SEQ ID NO:13, and KLLAEth SEQ ID NO:15. When 0.1% proline was used as a nitrogen source, a zone of complete growth inhibition was seen for the toxic peptides KLLEth, KLAEth, and KLLAEth for PB1X-9B(pOPT1) but not for PB1X-9B(pRS202) (FIG. 5; Table 1). Neither strain exhibited sensitivity to the toxic dipeptide or tripeptide AEth and KLEth when proline was used as a nitrogen source.

The peptides can be used as a carrier for biologically active molecules, like polyoxins, nikicomycins, neopolyoxins, the latter two being peptidyl-nucleotides, which can be synthetically altered.

Transport of Lys-Leu-Gly-[³H]Leu SEQ ID NO:7 in *S. cerevsuze* Transformants

Figure 5A:
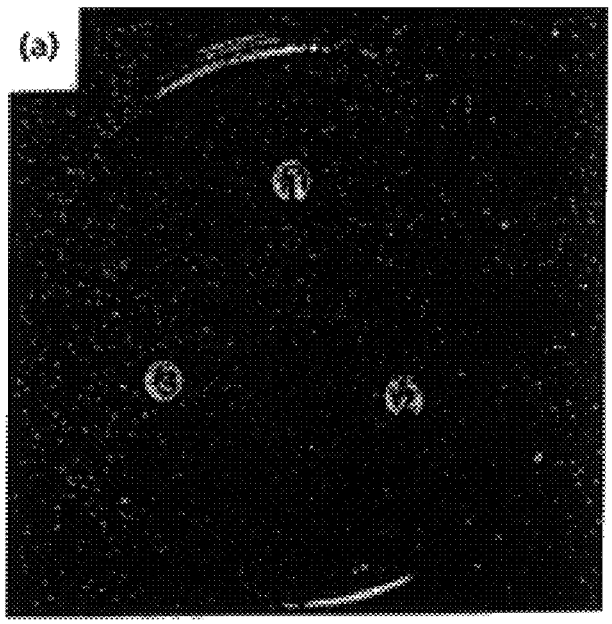
FIG. 5 is a toxic peptide inhibition assay. Sensitivity to the ethionine-containing peptides KLLAEth SEQ ID NO:15 (1) and KLLEth SEQ ID NO:12 (3) on a 0.1% proline medium was determined as described in Methods. (A) PB1X-9B (pRS202); (b) PB1X-9B(pOPT1).
Figure 5B:
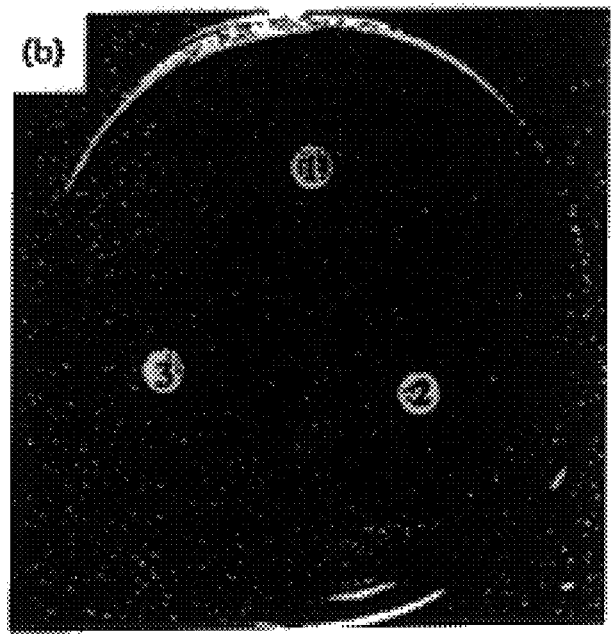
Figure 6A:
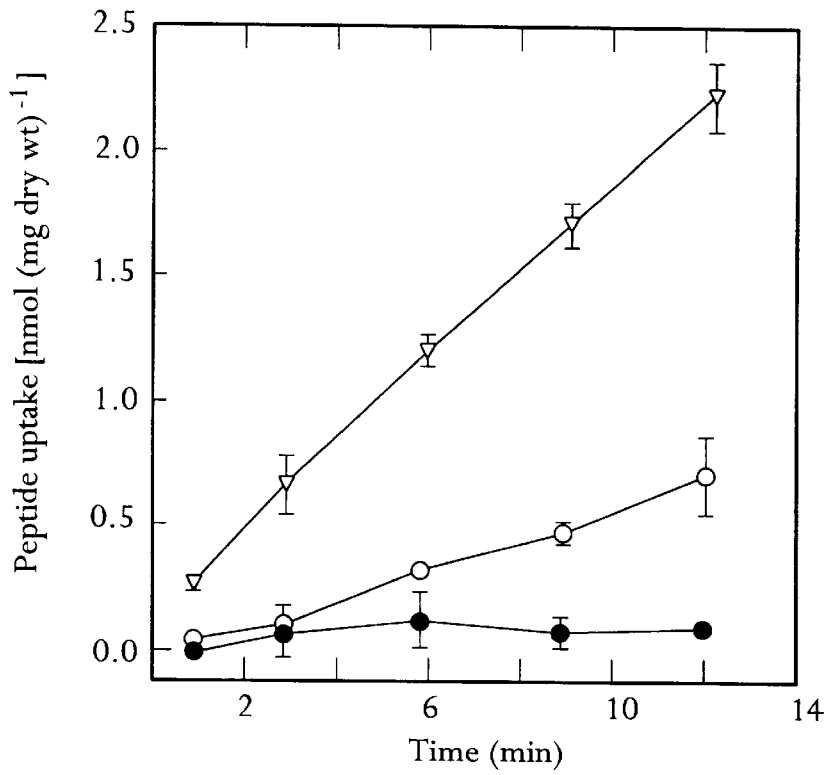
FIG. 6 is a peptide transport assay. Accumulation of KLG-[$^3$H]L was measured over a 12 min time course as described in Methods. *S. cerevisiae* PB1X-9B harbouring pRS202 (●) or pOPT1 (▽) and *C. albicans* SC5314 (○) were grown in SC-Ura medium with either ammonium sulfate (a) or 0.1% proline (b) as a nitrogen source.
Figure 6B:
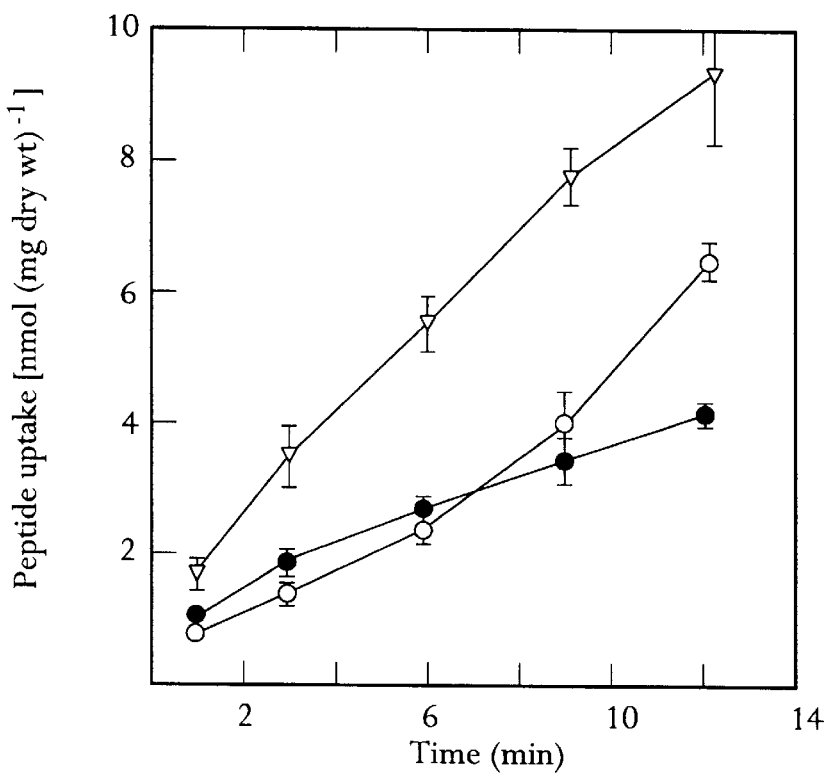

To determine if *S. cerevisiae* transformants harboring pOPT1 could accumulate a radiolabeled tetrapeptide, uptake assays were performed with the radiolabeled substrate KLG-[³H]L SEQ ID NO:7 with cells grown to log phase in SC-Ura with either ammonium sulfate or 0.1% proline as a nitrogen source. PB1X-9B(pOPT1) grown in SC with ammonium sulfate exhibited a significant uptake rate compared to no uptake by PB1X-9B(pRS202) (FIG. 6a). Furthermore, PB1X-9B(pOPT1) demonstrated a higher initial rate of uptake when compared to *C. albicans* SC5314 grown in the same medium. This higher initial rate can be explained by overexpression due to high copy number or alternatively by the lack of requisite regulatory elements which may be absent in the heterologous host. All three strains had a higher rate of initial uptake when grown in SC-Ura with 0.1% proline as a nitrogen source (FIG. 6b). PB1X-9B(pRS202) did accumulate the tetrapeptide KLGL SEQ ID NO:7 under these conditions but apparently not to a large enough extent to support growth on KLLG SEQ ID NO:6 or to exhibit sensitivity to KLLEth SEQ ID NO:12 or KLAEth SEQ ID NO:13 (Table 1; FIG. 5).

Figure 7:
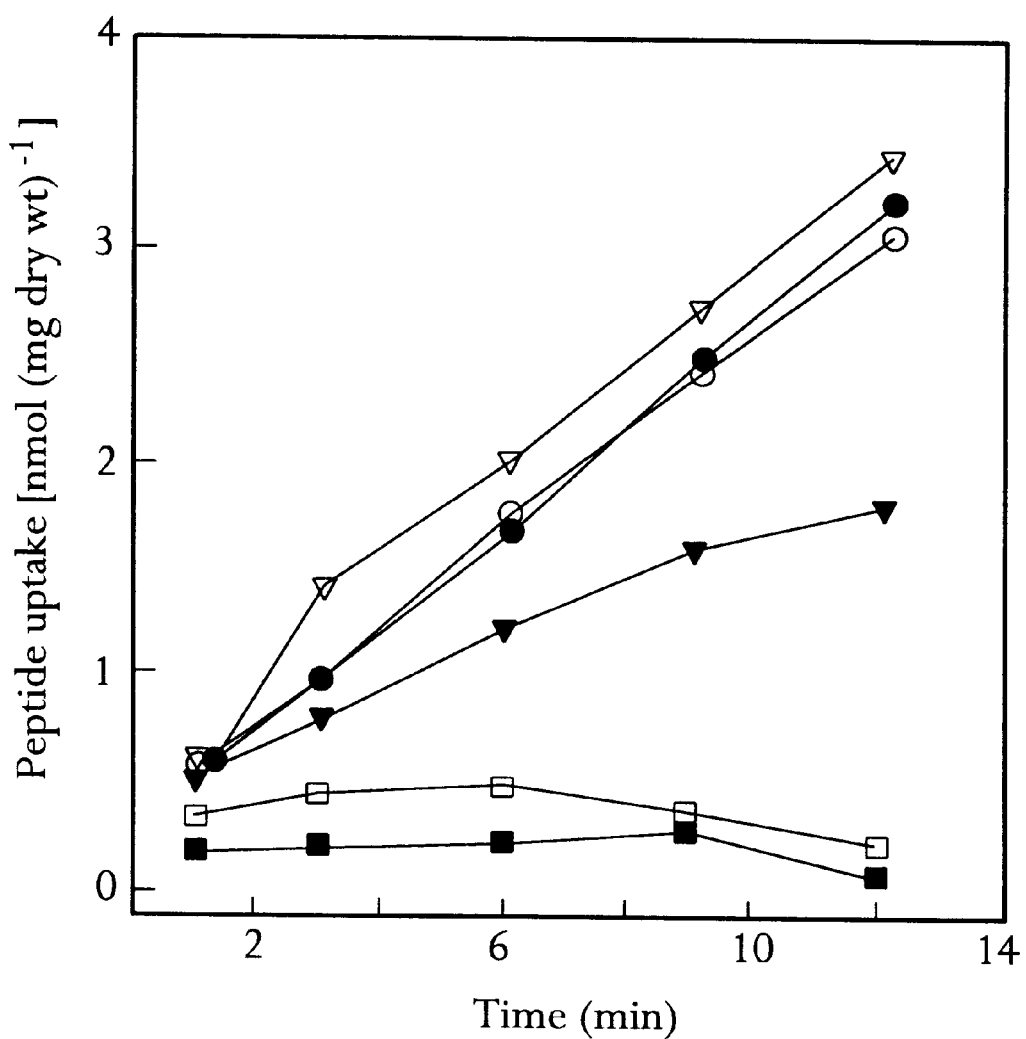
FIG. 7 is a peptide transport competition experiment. Accumulation of KLG-[$^3$H]L (○) was measured in the presence of a 10-fold molar excess of the competitors L (●), KL (▽), KLG (▼), KLLG SEQ ID NO:6 (■) over a 12 min time course.

To more rigorously determine the size constraints of the oligopeptide transporter, the accumulation of KLG-[³H]L SEQ ID NO:7 was measured in the presence of 10-fold molar excess of the competitors L, KL, KLG, KLLG SEQ ID NO:6, and KLLLG SEQ ID NO:8. SC-Ura with ammonium sulfate was chosen as the growth medium because under these growth conditions PB1X-9B(pOPT1) accumulated KLG-[³H]L SEQ ID NO:7 whereas PB1X-9B (pRS202) did not (FIG. 6a). As seen in FIG. 7, L and KL do not compete with the uptake of KLG-[³H]L SEQ ID NO:7 whereas competition was seen with KLLG SEQ ID NO:6 and KLLLG SEQ ID NO:8. The tripeptide KLG exhibited decreased competition in comparison to KLLG SEQ ID NO:6 or KLLLG SEQ ID NO:8 (FIG. 7) possibly due to a lower affinity, although this low level of KLG uptake is below the threshold to support full growth when used as an auxotrophic supplement. Uptake rates were calculated from a bestfit of the slope for each set of data. The uptake rate of KLG-[³H]L SEQ ID NO:7 in the presence of no competitor, L, or KL was 0.24, 0.25, and 0.26 nm/min/mg of dry weight, respectively. When KLG was used as a competitor the uptake rate was 0.12 nmoles/min/mg of dry weight which was approximately 50% of the no-competitor rate. The uptake rate approximated zero when KLLG SEQ ID NO:6 and KLLLG SEQ ID NO:8 were used as competitors.

DETAILED DISCUSSION OF THE PREFERRED EMBODIMENT

Characterization of the oligopeptide transport gene proceeded as follows. Three lines of evidence support the cloning of an oligopeptide transport gene from *C. albicans*. First, the plasmid pOPT1 conferred the ability to utilize the peptide KLLG to satisfy the leucine auxotrophic requirement of *S. cerevisiae* PB1X-9B when grown on a medium with a rich or poor nitrogen source. Secondly, the *S. cerevisiae* strain PB1X-9B was not sensitive to the toxic peptides KLLEth SEQ ID NO:12, KLAEth SEQ ID NO:13, or KLLAEth SEQ ID NO:15 when grown on a minimal medium with 0.1% proline as a nitrogen source but was sensitive when transformed with the plasmid pOPT1 (FIG. 5; Table 1). Similarly, a very faint zone of growth inhibition was seen for KLLEth SEQ ID NO:12, KLAEth SEQ ID NO:13, and KLLAEth SEQ ID NO:15 when PB1X-9B (pOPT1) but not PB1X-9B(pRS202) was grown in a medium containing ammonium sulfate. Finally, PB1X-9B (pRS202) had an initial uptake rate of zero for the radiolabelled substrate KLG-[³H]L SEQ ID NO:7 when grown on a media with ammonium sulfate whereas PB1X-9B(pOPT1) had a dramatically higher initial uptake rate (FIG. 6a). When the growth media contained proline as a nitrogen source, the initial uptake rate was 2.5 times higher for PB1X-9B (pOPT1) than for PB1X-9B(pRS202) (FIG. 6b). Furthermore, uptake was competed by KLLG SEQ ID NO:6 and KLLLG and to a lesser degree KLG SEQ ID NO:8 (FIG. 7). The fact that leucine did not compete with KLG-[³H]L SEQ ID NO:7 for uptake excluded the possibility that OPT1 coded for a secreted protease. Therefore, these studies demonstrated the cloning of an oligopeptide transporter from *C. albicans* capable of transporting tetra- and pentapeptides and to a lesser extent tripeptides.

Characterization of the protein product proceeded as follows. The predicted protein product of OPT1 did not show any significant homlogy to any members of the ABC superfamily or PTR family of transporters. Furthermore, a search of the Prosite (Bairoch, 1992) and Motifs (Devereux et al., 1984) databases for protein motifs did not reveal any previously identified functional domains common to transport proteins with the exception of potential glycosylation sites. However, are the twelve putative transmembrane domains separated by hydrophilic regions as well as the expression of transport activity in a heterologous host are suggestive of an integral membrane transporter.

Because three ORFs of significant homology as well as several Expressed Sequence Tags (data not shown) were identified, the possibility exists that OPT1 constitutes the first identified member of a new family of transporters. It is not excluded that one or more of these ORFs may encode proteins that have oligopeptide transport activity. Thus, one or more of these domains could be expressed from appropriate nucleotide sequences and retain a transporter function.

It was found that Opt1p is able to accommodate peptides of 3–5 residues. It is not excluded that oligopeptide activity would include peptides longer than pentapeptides. The protein encoded by OPT1 SEQ ID NO:2 is isolated in accordance with known protocols. Asubel et al., Current Protocols. As demonstrated by growth assays, halo assays, and competition experiments tetrapeptides were most readily transported by Opt1p. On the other hand, pentapeptides did enter the cell as demonstrated by sensitivity to KLLAEth SEQ ID NO:15 and supported by the competition between KLLLG SEQ ID NO:8 and KLG-[³H]L SEQ ID NO:7. However, KLLLG SEQ ID NO:7 was not able to support growth when used as a source of leucine possibly due to the inability of cellular peptidases to release leucine from this peptide. Similarly, KLG was able to compete slightly for entry into the cell with KLG-[³H]L SEQ ID NO:7, but KLG did not support growth and KLEth was not toxic. From these studies it can not be concluded that Opt1p has a lower affinity for tri- and pentapeptides than for tetrapeptides.

Nucleotide sequence analysis revealed the presence of a 58 nucleotide intron located within the 3Õ half of OPT1. The 5Õ splice site, 3Õ splice site, and branch point are identical to previously reported type II introns within fungi (Rymond and Rosbash, 1992). It is interesting to note that the di-/tripeptide transporter CaPTR2 also contains a small type II intron that is located within the 3Õ half of the gene. It has been suggested that introns play a regulatory role. However, a comparison of the two introns did not reveal any apparent consensus sequences that might be suggestive of a common regulatory element or of a common ancestory.

To date only one study has been published addressing the regulation of oligopeptide transport activity in *C. albicans*. Basrai et al., (1992) concluded that sensitivity to toxic oxalysine-containing tetra- and pentapeptides was not influenced by nitrogen source or by the presence of amino acid inducers. However, our findings suggest that when expressed in *S. cerevisiae*, OPT1 is regulated by nitrogen source. The discrepancy in results may be explained by differences in the levels of regulation or substrate specificity between the two different strains used in the studies , or alternatively by superimposition of a *S. cerevisiae* regulatory mechanism on the CaOPT1 gene expressed heterologously.

A search of the database using the BLAST algorithm identified three putative homologs of OPT1 SEQ ID NO:1. The ISP4 SEQ ID NO:3 gene from *S. pombe* exhibited the highest homology and was identified by Sato et al. (1994) through a subtractive hybridization experiment using RNA isolated from nitrogen starved and non-nitrogen starved cells. In *S. pombe*, nitrogen starvation induces meiosis and therefore this nitrogen-starvation/meiosis-inducing screen identified genes that were either induced during meiosis or regulated by the nitrogen catabolite repression system. Based upon the high homology between OPT1 SEQ ID NO:1 and ISP4 SEQ ID NO:3 and the established role of nitrogen regulation in many peptide transport systems, it was hypothesized that ISP4 SEQ ID NO:3 encodes an oligopeptide transporter that is regulated by nitrogen source.

The remaining two putative homologs were from *S. cerevisiae* and were identified during the genome sequencing project. Interestingly, few favorable conditions have been identified for oligopeptide transport activity in *S. cerevisiae*. As seen in FIG. 6, PB1X-9B(pRS202) when grown in a medium containing proline exhibited an initial uptake rate of KLG-[$^3$H]L SEQ ID NO:7 that was comparable to the initial uptake rate of PB1X-9B(pOPT1) when grown in a medium with ammonium sulfate. However, under these conditions PB1X-9B(pRS202) exhibited no sensitivity to the toxic tetrapeptides KLLEth SEQ ID NO:12 and KLAEth SEQ ID NO:13 and was not able to utilize the tetrapeptide KLLG SEQ ID NO:6 as a sole source of leucine, whereas PB1X-9B(pOPT1) did grow on KLLG SEQ ID NO:6 and exhibited slight sensitivity to the toxic peptides KLLEth SEQ ID NO:12 and KLAEth SEQ ID NO:13. This discrepancy in results could be explained by an uptake rate exhibited by PB1X-9B(pRS202) that may not necessarily be reflective of total peptide accumulation over the prolonged incubation times necessary for growth and sensitivity assays.

MATERIALS AND METHODS

Strains, Vectors and Media

The strains used herein were *S. cerevisiae* PB1X-9B (MATa ura3-52 leu2-3,112 lys1-1 his4-38 ptr2-2) (Perry et al., 1994) and *C. albicans* SC5314 (Fonzi and Irwin, 1993).

*C. albicans* and *S. cerevisiae* cells were maintained on YBPD medium (2% dextrose, 1% Yeast Extract, 2% Peptone, and 1.5% agar). The minimal medium used for most studies was made by adding 10 ml of 10× filter sterilized YNB (Yeast Nitrogen Base, Difco) with ammonium sulfate and without amino acids to 90 ml of sterile water containing 2 g glucose and auxotrophic supplements (Sherman et aM, 1986). For those experiments where proline was used as a sole nitrogen source YNB without amino acids and without ammonium sulfate was supplemented with 0.1% prolne. The mutant strain *S. cerevisiae* PB1X-9B was grown in Synthetic Complete Medium (SC) which consisted of minimal medium with histidine, uracil, lysine and leucine. *S. cerevisiae* PB1X-9B transformed with pRS202 based plasmids was grown on SC lacking uracil (SC-Ura).

The *C. albicans* library used for cloning OPT1 SEQ ID NO:1 was provided by Gerry Fink (Liu et al., 1994). The library was created by partially digesting *C. albicans* strain 1006 genomic DNA (Goshom and Sherer, 1989) with Sau3A and cloning the resulting fragments (>4 kb) into the SalI site of pRS202, a URA3/2 μ based plasmid (Christianson et al., 1992).

Peptide medium consisted of minimal medium supplemented with auxotrophic requirements minus the amino acid Seucine plus 100 μM of one of the following peptidest Lysyl-Leucine (KL), Lysyl-Leucyl-Glycine (KLG), Lysyl-Leucyl-Leucyl-Glycine (KLLG) SEQ ID NO:6, Lysyl-Leucyl-Glycyl-Leucine (KLGL) SEQ ID NO:7, or Lysyl-Leucyl-Leucyl-Leucyl-Glycine (KLLLG) SEQ ID NO:8. Abbreviations for toxic peptides and amino acids used herein are as follows: Ethionine (Eth), Alanyl-Ethionine (AEth), Leucyl-Ethionine (LEth), Lysysl-Leucyl-Ethionine (KLEth), Lysyl-Leucyl-Leucyl-Ethionine (KLLEth) SEQ ID NO:12, Lysysl-Leucyl-Alanyl-Ethionine (KLAEth) SEQ ID NO:14, and Lysyl-Leucyl-Leucyl-Leucyl-Ethionine (KLLLEth) SEQ ID NO:13. All amino acids were in the L configuration.

Enzymes, Chemicals and Reagents

Restriction endonucleases, T4 DNA ligase, T4 DNA polymerase, and alkaline phosphatase were purchased from New England BioLabs or Promega and were used according to the manufacturers specifications.

Synthesis of Radioactive Lys-Leu-Gly-[$^3$H]Leu SEQ ID NO:7

KLGL SEQ ID NO:7 was prepared by conventional automated solid phase peptide synthesis on an Applied Biosystems Model 433A synthesizer. Peptide was cleaved from the resin with trifluoroacetic acid (TFA) and purified using a $C_{18}$ reversed phase column (19×300 mm) to >99% homogeneity with a 5 to 20% linear gradient of acetonitrile in water over 60 minutes. The product was verified using mass spectrometry [(M$^+$+1)=430.2; calculated=429.6].

Tritiated KLGL (Lys-Leu-Gly-[$^3$H]Leu SEQ ID NO:7) was prepared by solution phase peptide synthesis as follows. BocLys(Boc)-Leu-Gly-OH (5.2 mg; 10 μmol) was dissolved in 108 μl of a 0.092 μmol/μl solution of N-hydroxysuccinimide (10 μmol) in dry dioxane. Dicyclohexylcarbodiimide (10 μmol in 57 μl) in dry dioxane was added and the reaction mixture was stirred for one hour at ambient temperature. Leu (0.65 mg, 5 μmol), dissolved in 1 ml of water, was added to radioactive leucine (American Radiolabeled Chemicals, Inc., St. Louis, Mo.; Specific Activity 60 Ci/mmol; Concentration 1 mCi/ml in 2% ethanol). This solution was evaporated to dryness, redissolved in 250 μl of water/dioxane (4:1) containing N-methyl morpholine (50 μmol) and the solution containing the activated tripeptide was added. The resulting reaction mixture was stirred for 6 hours at ambient temperature, 5.5 ml of TFA was then added, and after 5 minutes the reaction mixture was evaporated to dryness. The residue was redissolved in 500 μl of water, injected onto a Waters μBondapack $C_{18}$ column (7.8×300 mm) and eluted isocratically using 5% acetonitrile in water, containing 0.025% TFA. Product elluting at the KLGL SEQ ID NO:7 position was collected, evaporated, redissolved in water (200 μl) and analyzed by high pressure liquid chromatography (HPLC) and on silica thin layers using a Butanol:Acetic acid:water (4:1:5) mobile phase. TLC plates were exposed to film overnight at −80 C. and developed to show one radioactive spot with the mobility of the desired tetrapeptide. KLG-[$^3$H]L SEQ ID NO:7 was >97% pure according to HPLC. Specific radioactivity was 90 mCi/mmol. Peptide was diluted with nonradioactive KLGL SEQ ID NO:7 as required.

DNA Manipulations

Small scale plasmid DNA preparations from *E. coli* transformants were performed as described in Sambrook et al. (1989). Plasmid DNA from *S. cerevisiae* transformants was isolated as described previously (Ward, 1990). Whole cell DNA from *C. albicans* was obtained by the procedure described by Ausubel et al.(1990).

Yeast transformations were done using the procedure described by Gietz et al. (1991) and plates were incubated at 30 $_i$C. for 4 days or longer.

For Southern analyses whole cell DNA was digested with restriction enzymes and electrophoresed on 1.0% agarose gels. Southern blotting was done as described in Sambrook et al. (1989). Hybridization was performed at 60° C. for twelve hours in a Hybritube (Gibco BRL) followed by two washes of 1×SSC, 0.1% SDS at 42° C. and two washes of 0.1×SSC and 0.1% SDS at 60° C. The probe used for Southern blots was generated via PCR using the primers LC2 (5'GCATGGATTGTTCCTGACTGG3') (SEQ ID NO:10) and FT2 (5'CCAATACCAAACAAATGAAGGC3') (SEQ ID NO:11). The product was 408 bp in length and its position within the OPT1 ORF is depicted in FIG. 1. The Southern blot displayed in FIG. 2 was processed using the program Adobe Photoshop.

For plasmid curing experiments *S. cerevisiae* transformants were grown nonselectively in YEPD broth for about 40 generations. Cells were then plated on YEPD plates to obtain isolated colonies which were picked, washed with water, resuspended at 5×10$^6$ cells/ml in sterile water, and spotted onto the appropriate peptide medium.

The nucleotide sequence of the 3.8 kb insert in plasmid pOPT1 was generated through automated cycle sequencing using an ABI 373A Automated sequencer (Smith et al., 1986). The insert of pOPT1 was digested with either TaqI or Sau3A, subcloned into M13, and ssDNA isolated as a template for sequencing from randomly chosen plaques. The sequenced fragments were assembled using the software DNASTAR and the remaining gaps were filled using properly placed primers. Primers were purchased from Bioserve Biotechnologies. Final assembly was performed using Autoassembler from ABI.

Growth and Transport Assays

Growth assays to determine the phenotype of the cells were done as described by Island et al. (1991). Briefly, 3 μl of culture from a suspension of 5×10$^6$ cells/ml were spotted to the surface of the medium and plates were incubated at 30 $_i$C for 4–7 days.

Uptake of KLG-[$^3$H]L SEQ ID NO:7 was determined using a protocol for uptake of dipeptides as described by Basrai et al. (1995) with a few modifications. *S. cerevisiae* cultures were grown overnight to exponential phase in SC-Ura medium. Cells were harvested by centrifugation, and resuspended in 2% glucose at a cell density of 2×10$^8$ cells/ml. Two hundred and fifty microliters of cell suspension were added to an equal volume of an uptake assay reaction mixture and incubated at 30$_i$C. The final concentrations of the components in the uptake assay solution were: glucose (2%, w/v), 10 mM sodium citrate/potassium phosphate buffer (pH 5.0), and KLG-[$^3$H]L SEQ ID NO:7 (150 μM; 8.5 mCi/mmol). Competition experiments were done in the presence of either 1.5 mM L, KL, KLG, KLLG SEQ ID NO:6, or KLLLG SEQ ID NO:8. At various time points, 90 μl portions were removed and filtered through a membrane. The yeast cells retained on the filter were washed twice with ice-cold distilled water, once with room temperature distilled water, and the residual radioactivity was measured by liquid scintillation. There was no peptide adsorption to the cell surface or sticking to filters since at 0$_i$ C the counts were at background level. The uptake results, calculated on the basis of 50% counting efficiency (determined using L-[$^3$H] lysine as a standard, and the specific activity of the peptide), were expressed as nmol of peptide uptake per minute per mg cell dry weight.

Sensitivity Assays

Sensitivity to ethionine, a toxic methionine analog, and ethionine-containing peptides was determined by the method described by Island et al. (1987). Cells were grown overnight to exponential phase of growth in SC, washed, and resuspended at 5×10$^6$ cells /ml in sterile water. One ml of this cell suspension was added to 3 ml molten Noble agar (0.8% final concentration) and overlayed on 20 ml of the same medium used to prepare the inoculum. A disk (6 mm diameter, Difco) was placed on the plate and 0.38 μmoles of the compounds to be tested were applied to the disks. Zones of inhibition were measured after 24–48 hr incubation at 30 $_i$C. Each test comprised at least three independent assays and the results represented in the Tables are means of the values obtained. Maximum variation between the zones of inhibition measured for each test were $^2$3 mm. A value of 7 mm for the diameter of zone of inhibition represents a minimal growth inhibition value as the disk diameter was 6 mm. Photodocumentation of sensitivity assays was done with a Umax Scanner and processed through Adobe Photoshop.

REFERENCES

All references are incorporated herein by reference in their entirety.

Altshul, S. F., Gish, W., Miller, W., Myers, E. W., & Lipman, D. J. (1990). Basic local alignment search tool. *J. Mol. Biol.* 215:403–410.

Ausubel, F. M., Brent, R., Kingston, R., Moore, D. D., Seidman, J. G.,. Smith, J. A., & Struhl, K. (1990). *Current Protocols in Molecular Biology* 2. New York: Wiley Interscience, Inc.

Bairoch. (1992). PROSITE: a dictionary of sites and patterns in proteins. *Nucl. Acids Res.* 20: 2013–2018.

Basrai, M. A., Lubkowitz, M. A., Perry, J. R., Miller, D., Krainer, E., Naider, F., & Becker, J. M. (1995). Cloning of a *Candida albicans* peptide transport gene. *Microbiology UK* 141: 1147–1156.

Basrai, M. A., Zhang, H-L., Miller, D., Naider, F., & Becker, J. M. (1992). Toxicity of oxalysine and oxalysine-containing peptides against *Candida albicans:* regulation of peptide transport by amino acids. *J. Gen. Microbiol.* 138:2353–2362.

Becker, J. M. & Naider, F. (1995). Fungal peptide transport as a drug delivery system. In *Peptide Based Drug Design: Controlling Transport and Metabolism*, pp. 369–384. Edited by M. Taylor and G. Amidon. Washington, DC: American Chemical Society.

Christianson, T. W., Sikorski, R. S., Dante, M., Shero, J. H., & Heiter, P. (1992). Multifunctional yeast high copy number shuttle vectors. *Gene* 110: 119.

Cundell, D. R., Pearce, B. J., Sandros, J., Naughton, A. M., & Masure, H. R. (1995). Peptide permeases from *Streptococcus pneumoniae* affect adherence to eukaryotic cells. *Infection and Imunnity* 63: 2493–2498.

Devereux, Haerbili, J. P., & Smithies, O. (1984). A comprehensive set of sequence analysis programs for the VAX. *Nucl. Acids Res.* 12:387–395.

Feng, D.-F., & Doolittle, R. F. (1987). Progressive sequence alignment as a prerequisite to correct phylogenetic trees. *J. Mol. Evol.* 25:351–360.

Fonzi, W. A. & Irwin, M. Y. (1993). Isogenic strain construction and gene mapping in *Candida albicans*. *Genetics* 134:717–728.

Gietz, D., Andrew, J., Woods, R., & Schiestl, R. (1991). Improved methods for high efficiency transformation of intact yeast cells. *Nucl. Acids Res.* 20:1425.

Goshorn, A. G., & Sherer, S. (1989). Genetic analysis of prototrophic natural variants of *Candida albicans*. *Genetics* 123: 667–673.

Hagting, A., Kunji, E. R., Leenhouts, K. J., Poolman, B., & Konings, W. N. (1994). *J. Biol. Chem.* 269:11391–11399.

Higgins, C. F. (1992). ABC transporters: from microorganisms to man. *Annu. Rev. Cell Biol.* 8:67–113.

Island, M. D., Naider, F., & Becker, J. M. (1987). Regulation of dipeptide transport in *Saccharonzyces cerevisiae* by micromolar amino acid concentrations. *J. Bacteriol.* 169:2132–2136.

Island, M. D., Perry, J. R., Naider, F., & Becker, J. M. (1991). Isolation and characterization of S. cerevisiaeÊ- mutants deficient in amino acid-inducible peptide transport. *Curr. Genetics* 20:457–463.

Liu, H., Kohler, J., & Fink, G. (1994). Suppression of hyphal formation in *Candida albicans* by mutation of a STE12 homolog. *Science* 266: 1723–1725.

McCarthy, J. P., L. J. Nisbet, J. C. Boelun, & Kingsbury, W. D. (1985). Multiplicity of peptide permeases in *Candida albicans*: Evidence from novel chromophoric peptides. *J. Bacteriol.* 162:1024–1029.

Milewski, S., Andruskiewicz, R., & Borowski, E. (1988). Substrate specificity of peptide permeases in *Candida albicans*. *FEMS Microbiol.Letters* 50:73–78.

Omaha, T., Suzuki, T., Mori, M., Osawa, S., Ueda, T., Watanabe, K., & Nakase, T. (1993). Non-universal decoding of the leucine codon CUG in several Candida species. *Nucl. Acids. Res.* 21: 4039–4045.

Parra-Lopez, C., Baer, M. T., & Groisman, E. A. (1993). Molecular genetic analysis of a locus reqquired for resistance to antimicrobial peptides in *Salmonella typhimurium*. *EMBO.* 12: 4053–4062.

Payne, J. W. & Shallow, D. A. (1985). Studies on drug targeting in the pathogenic fungus *Candida albican*: peptide transport mutants resistant to polyoxins, nikkomycins and bacilysin. *FEMS Micriobiol. Letters* 28: 55–60.

Payne, J. W. & Smith, M. W. (1994). Peptide transport by micro-organisms. *Adv. Microbiol. Phys.* 36: 1–80.

Perry, J. R., Basrai, M. A., Steiner, H-Y., Naider, F., & Becker, J. M. (1994). Isolation and Characterization of a *Saccharomyces cerevisiae* Peptide Transport Gene. *Mol. Cell. Biol.* 14: 104–115.

Rymond, B. C., & Rosbash, M. (1992). Yeast pre-mRNA splicing. p.143–192. in E. W. Jones, J. R. Pringle, and J. R. Broach (ed.), *The Molecular and Cellular Biology of the Yeast Saccharomyces*. Cold Spring Harbor Press, Cold Spring Harbor, N.Y.

Sambrook, J., Fritsch, E. F., & Maniatis, T. (1989). *Molecular Cloning, A Laboratory Manual*. Second Edition. Cold Spring Harbor Laboratory, Cold Spring Harbor, N.Y.

Sato, S., Suzuki, H., Widyastuti, U., Hotta, Y., & Tabata, S. (1994). Identification and characterization of genes induced during sexual differentiation in *Schizosaccharomyces pombe*. *Current Genetics* 26: 31–37.

Sherman, F., Fink, G. R., & Hicks, J. B. (1986). In *Methods of Yeast Genetics*. Cold Spring Harbor Laboratory, Cold Spring Harbor, N.Y.

Smith, L. M., Sander, J. Z., Kaiser, R. J., Hughes, P., Dodd, C., Connel, C. R., Heiner, C., Kent, S. B., & Hood, L. E. (1986). Flourescence detection in automated DNA sequence analysis. *Nature.* 321:674–679.

Steiner, H-Y., Naider, F., & Becker, J. M. (1995). The PTR family: a new group of peptide transporters. *Mol. Microbiol.* 16: 825–834.

Steiner, H-Y., Song, W., Naider, F., Zhang, L., Stacey, G., & Becker, J. M. (1994). An Arabidopsis peptide transporter is a member of a new class of membrane transport proteins. *Plant Cell* 6: 1289–1299.

Song, W., Steiner, H-Y., Zhang, L., Naider, F., Stacey, G., & Becker, J. M. (1996). Cloning of a second Arabidopsis peptide transport gene. *Plant Physiol.* 110: 171–178.

Ward, A. C. (1990). Single step purification of shuttle vectors from yeast for high frequency back-transformation into *E. coli. Nucl. Acids Res.* 18: 5319.

Yadan, J. C., Gonneau, M., Sarthou, P., & Le Goffic, F. (1984). Sensitivity to nikkomycin Z in *Candida albicans*: Role of peptide permeases. *J. of Bacteriol.* 160: 884–888.

---

What is claimed is:

1. An isolated oligopeptide membrane transporter which is not a member of the Peptide Transport (PTR) or ATP Binding Cassette (ABC) families.

2. The oligopeptide membrane transporter of claim 1 which is from *Candida albicans*.

3. The oligopeptide membrane transporter of claim 1 which is competent to transport pentapeptides.

4. The oligopeptide membrane transporter of claim 3 which is competent to transport the pentapeptides in a heterologous host.

5. The oligopeptide membrane transporter of claim 4 wherein the pentapeptides are toxic.

6. The oligopeptide membrane transporter of claim 1 which is encoded by a nucleic acid sequence which comprises SEQ ID NO:1.

7. The oligopeptide membrane transporter of claim 6 which is encoded by SEQ ID NO:1.

8. The oligopeptide membrane transporter of claim 1 which is a member of the Oligopeptide Transporter family.

9. The oligopeptide membrane transporter of claim 1 which is competent to transport oligopeptides comprising at least five peptides.

10. The oligopeptide membrane transporter of claim 9 which is from *Candida albicans*.

* * * * *

SEQUENCE LISTING

```
<160> NUMBER OF SEQ ID NOS: 15

<210> SEQ ID NO 1
<211> LENGTH: 3872
<212> TYPE: DNA
<213> ORGANISM: C. albicans
<220> FEATURE:
<221> NAME/KEY: CDS
<222> LOCATION: (481..2106, 2165..2887)

<400> SEQUENCE: 1
gatcatgtgg ctaaaaattc atatggcttt atgctgtggc ttcagctcta ctgataattg      60
atatctttat tcctatacat aaatattaaa gccacttgat tattgctcat agggccaaaa     120
aaacaaaaag atgcagaacc atctaaagtt ttgttttgtg tttgctattt tgtgcctagt     180
gagattaaat tagttatctt ttcatgacaa aaatccttta gactacttt tattccattt     240
```

-continued

```
gtttggttta cgattatcaa tcgtcatagt tcaatttgta aaattttatc ttttcaatcc    300 caaaccttt aaatagtcag taatttctct cataggaatt tcaagtttcc acttttttt     360 gtcttccttc tattttcttt ttataagttt actgttcgt gaaatattat tcatttgtat    420
tatttttact aagtcaacca ctattgattc cattcctaac acttattata agtacttact   480
```

| | | | | | | | | | | | | | | | | |
|---|---|---|---|---|---|---|---|---|---|---|---|---|---|---|---|---|
| atg | gac | aaa | ata | agg | gca | gta | att | agt | gga | ggt | gag | aaa | cct | ccc | gtt | 528 |
| Met | Asp | Lys | Ile | Arg | Ala | Val | Ile | Ser | Gly | Gly | Glu | Lys | Pro | Pro | Val | |
| 1 | | | | 5 | | | | | 10 | | | | | 15 | | |

| gac | act | gac | aac | gat | cac | aac | aca | gac | ttt | gag | gct | gac | aga | aaa | atg | 576 |
|---|---|---|---|---|---|---|---|---|---|---|---|---|---|---|---|---|
| Asp | Thr | Asp | Asn | Asp | His | Asn | Thr | Asp | Phe | Glu | Ala | Asp | Arg | Lys | Met | |
| | | | 20 | | | | | 25 | | | | | 30 | | | |

| cca | gat | ttg | gat | att | gta | gtt | tcc | aaa | tca | caa | gaa | ttt | gac | caa | gtc | 624 |
|---|---|---|---|---|---|---|---|---|---|---|---|---|---|---|---|---|
| Pro | Asp | Leu | Asp | Ile | Val | Val | Ser | Lys | Ser | Gln | Glu | Phe | Asp | Gln | Val | |
| | | 35 | | | | | 40 | | | | | 45 | | | | |

| acc | tcc | cac | ttg | gtt | aat | gat | att | atg | gaa | gat | gaa | tat | gct | gct | gtc | 672 |
|---|---|---|---|---|---|---|---|---|---|---|---|---|---|---|---|---|
| Thr | Ser | His | Leu | Val | Asn | Asp | Ile | Met | Glu | Asp | Glu | Tyr | Ala | Ala | Val | |
| | 50 | | | | | 55 | | | | | 60 | | | | | |

| cat | gtt | gaa | gat | gat | tct | cct | tat | cca | gaa | gtt | aga | gca | gct | gtt | cct | 720 |
|---|---|---|---|---|---|---|---|---|---|---|---|---|---|---|---|---|
| His | Val | Glu | Asp | Asp | Ser | Pro | Tyr | Pro | Glu | Val | Arg | Ala | Ala | Val | Pro | |
| 65 | | | | | 70 | | | | | 75 | | | | | 80 | |

| tct | act | gac | gac | cca | act | tta | cct | caa | aat | acc | att | aga | gcc | tgg | gtt | 768 |
|---|---|---|---|---|---|---|---|---|---|---|---|---|---|---|---|---|
| Ser | Thr | Asp | Asp | Pro | Thr | Leu | Pro | Gln | Asn | Thr | Ile | Arg | Ala | Trp | Val | |
| | | | 85 | | | | | 90 | | | | | 95 | | | |

| att | ggt | ttg | ata | ttg | act | acg | gtt | ggt | tgt | ggt | atg | aat | atg | ttg | ttc | 816 |
|---|---|---|---|---|---|---|---|---|---|---|---|---|---|---|---|---|
| Ile | Gly | Leu | Ile | Leu | Thr | Thr | Val | Gly | Cys | Gly | Met | Asn | Met | Leu | Phe | |
| | | 100 | | | | | 105 | | | | | 110 | | | | |

| agt | ttc | cat | agt | ccc | tca | ttt | gct | atc | acc | act | ttt | gtc | aca | tcc | att | 864 |
|---|---|---|---|---|---|---|---|---|---|---|---|---|---|---|---|---|
| Ser | Phe | His | Ser | Pro | Ser | Phe | Ala | Ile | Thr | Thr | Phe | Val | Thr | Ser | Ile | |
| | 115 | | | | | 120 | | | | | 125 | | | | | |

| ttg | gct | tgg | cca | att | ggg | aac | ttt | tgg | gca | tgg | att | gtt | cct | gac | tgg | 912 |
|---|---|---|---|---|---|---|---|---|---|---|---|---|---|---|---|---|
| Leu | Ala | Trp | Pro | Ile | Gly | Asn | Phe | Trp | Ala | Trp | Ile | Val | Pro | Asp | Trp | |
| 130 | | | | | 135 | | | | | 140 | | | | | | |

| aag | att | ttt | ggt | gct | tcg | tta | att | cca | ggt | cca | ttc | aac | gtt | aaa | gaa | 960 |
|---|---|---|---|---|---|---|---|---|---|---|---|---|---|---|---|---|
| Lys | Ile | Phe | Gly | Ala | Ser | Leu | Ile | Pro | Gly | Pro | Phe | Asn | Val | Lys | Glu | |
| 145 | | | | | 150 | | | | | 155 | | | | | 160 | |

| cat | act | atc | atc | act | att | atg | gcc | aac | gtt | tct | ttt | ggt | act | ggt | gcc | 1008 |
|---|---|---|---|---|---|---|---|---|---|---|---|---|---|---|---|---|
| His | Thr | Ile | Ile | Thr | Ile | Met | Ala | Asn | Val | Ser | Phe | Gly | Thr | Gly | Ala | |
| | | | 165 | | | | | 170 | | | | | 175 | | | |

| gca | tat | gcc | aca | gat | atc | ttg | ctt | gca | caa | aat | atg | ttt | tat | aaa | tca | 1056 |
|---|---|---|---|---|---|---|---|---|---|---|---|---|---|---|---|---|
| Ala | Tyr | Ala | Thr | Asp | Ile | Leu | Leu | Ala | Gln | Asn | Met | Phe | Tyr | Lys | Ser | |
| | | | 180 | | | | | 185 | | | | | 190 | | | |

| aat | ttt | ggt | tgg | ggg | tac | aat | tta | tta | ctt | atc | tgg | agt | acc | caa | tgt | 1104 |
|---|---|---|---|---|---|---|---|---|---|---|---|---|---|---|---|---|
| Asn | Phe | Gly | Trp | Gly | Tyr | Asn | Leu | Leu | Leu | Ile | Trp | Ser | Thr | Gln | Cys | |
| | | 195 | | | | | 200 | | | | | 205 | | | | |

| att | ggg | ttt | gct | ttc | gga | gct | gtt | atg | aga | aga | ttt | gtt | gtt | gac | agt | 1152 |
|---|---|---|---|---|---|---|---|---|---|---|---|---|---|---|---|---|
| Ile | Gly | Phe | Ala | Phe | Gly | Ala | Val | Met | Arg | Arg | Phe | Val | Val | Asp | Ser | |
| | 210 | | | | | 215 | | | | | 220 | | | | | |

| cca | ggc | gcc | atc | tgg | ccc | ctg | aat | ttg | gtc | acc | gca | aca | ttc | ttg | act | 1200 |
|---|---|---|---|---|---|---|---|---|---|---|---|---|---|---|---|---|
| Pro | Gly | Ala | Ile | Trp | Pro | Leu | Asn | Leu | Val | Thr | Ala | Thr | Phe | Leu | Thr | |
| 225 | | | | | 230 | | | | | 235 | | | | | 240 | |

| aat | atg | cac | att | aac | gaa | aac | cac | act | gct | aat | ggc | tgg | aaa | att | tct | 1248 |
|---|---|---|---|---|---|---|---|---|---|---|---|---|---|---|---|---|
| Asn | Met | His | Ile | Asn | Glu | Asn | His | Thr | Ala | Asn | Gly | Trp | Lys | Ile | Ser | |
| | | | | 245 | | | | | 250 | | | | | 255 | | |

| cgt | ctt | gca | ttt | ttc | gtg | atc | gtg | ttt | gtt | gcc | tca | ttt | gtt | tgg | tat | 1296 |
|---|---|---|---|---|---|---|---|---|---|---|---|---|---|---|---|---|
| Arg | Leu | Ala | Phe | Phe | Val | Ile | Val | Phe | Val | Ala | Ser | Phe | Val | Trp | Tyr | |
| | | | 260 | | | | | 265 | | | | | 270 | | | |

| tgg | ttc | cca | ggt | tat | att | ttc | cag | gct | tta | tcg | tat | ttt | tct | tgg | atc | 1344 |
|---|---|---|---|---|---|---|---|---|---|---|---|---|---|---|---|---|
| Trp | Phe | Pro | Gly | Tyr | Ile | Phe | Gln | Ala | Leu | Ser | Tyr | Phe | Ser | Trp | Ile | |

-continued

```
              275                 280                 285
acc tgg att aaa cca aac att gtc att atc aat caa gtt ttc ggt tct    1392
Thr Trp Ile Lys Pro Asn Ile Val Ile Ile Asn Gln Val Phe Gly Ser
    290                 295                 300 tca tct ggg tta ggt atg att cct aac aac att gcc ttg gac tgg aac    1440
Ser Ser Gly Leu Gly Met Ile Pro Asn Asn Ile Ala Leu Asp Trp Asn
305                 310                 315                 320 caa att gca ggg tat att ggg tct cca ttg att cca cca gct agt gtt    1488
Gln Ile Ala Gly Tyr Ile Gly Ser Pro Leu Ile Pro Pro Ala Ser Val
                325                 330                 335 att gct aca att ttt gga tcc att gtg ctt att ttc tgg att gtt gtg    1536
Ile Ala Thr Ile Phe Gly Ser Ile Val Leu Ile Phe Trp Ile Val Val
            340                 345                 350 cca gct att cac tat tcc aac act tgg tac tcc caa tac ttg cca atc    1584
Pro Ala Ile His Tyr Ser Asn Thr Trp Tyr Ser Gln Tyr Leu Pro Ile
        355                 360                 365 tca tct act gga tcg ttt gat agg ttc caa caa act tat aat gtg tca    1632
Ser Ser Thr Gly Ser Phe Asp Arg Phe Gln Gln Thr Tyr Asn Val Ser
    370                 375                 380 aaa att atc gac cat aaa act tta tca ttc aat gaa gcg gaa tac aaa    1680
Lys Ile Ile Asp His Lys Thr Leu Ser Phe Asn Glu Ala Glu Tyr Lys
385                 390                 395                 400 aag tac ttc cct ttg ttt tta tcc acc acc ttt gcc att tcc tat ggg    1728
Lys Tyr Phe Pro Leu Phe Leu Ser Thr Thr Phe Ala Ile Ser Tyr Gly
                405                 410                 415 cta tca ttt gcc tcc att tta gcc act ata aca cac acc att tgc ttc    1776
Leu Ser Phe Ala Ser Ile Leu Ala Thr Ile Thr His Thr Ile Cys Phe
            420                 425                 430 cat gga cgt gag ctt atc gca tcg ttg aag gcc aaa gaa aaa caa gat    1824
His Gly Arg Glu Leu Ile Ala Ser Leu Lys Ala Lys Glu Lys Gln Asp
        435                 440                 445 gtt cac aat aga tta atg aaa gca tac aaa cca gtg cct gaa tgg tgg    1872
Val His Asn Arg Leu Met Lys Ala Tyr Lys Pro Val Pro Glu Trp Trp
    450                 455                 460 tac cta gtt gtc tcc ttg gtc ttt ttc gtt atg tcc ata gcc acc gta    1920
Tyr Leu Val Val Ser Leu Val Phe Phe Val Met Ser Ile Ala Thr Val
465                 470                 475                 480 cgt gct tgg cct act gaa atg cca gta tgg ggg tta gtt ttt gct ctt    1968
Arg Ala Trp Pro Thr Glu Met Pro Val Trp Gly Leu Val Phe Ala Leu
                485                 490                 495 atc atc gct atc ata ttt tta tta ccc gtt gct atc att tat gca aaa    2016
Ile Ile Ala Ile Ile Phe Leu Leu Pro Val Ala Ile Ile Tyr Ala Lys
            500                 505                 510 acg aat aat gct gtt ggt tta aac gtt gta acc gag ttc atc gtg ggc    2064
Thr Asn Asn Ala Val Gly Leu Asn Val Val Thr Glu Phe Ile Val Gly
        515                 520                 525 tac gta cta ggt gga cgt ccc cta tgt atg atg ttg ttc aag             2106
Tyr Val Leu Gly Gly Arg Pro Leu Cys Met Met Leu Phe Lys
    530                 535                 540 gcatgtatta gaatttgcag atcataatca gtcagtttac taacctaatt ttgaatag    2164 acc ttc gga tac atc act aat aac caa gct gtt act ttt gtg cag gat    2212
Thr Phe Gly Tyr Ile Thr Asn Asn Gln Ala Val Thr Phe Val Gln Asp
                545                 550                 555 atg aaa ctt ggg cac tac atg aaa ata gat ccg cgc act ttg ttt tgg    2260
Met Lys Leu Gly His Tyr Met Lys Ile Asp Pro Arg Thr Leu Phe Trp
            560                 565                 570 gcg cag ttt gct gct acc ata tgg gga tcg tta gtt cag atc gca gtt    2308
Ala Gln Phe Ala Ala Thr Ile Trp Gly Ser Leu Val Gln Ile Ala Val
        575                 580                 585                 590
```

-continued

| | | |
|---|---|---|
| ttg gag tgg gcc tat ggt gca atc gac aat ttg tgt gct gct gac caa<br>Leu Glu Trp Ala Tyr Gly Ala Ile Asp Asn Leu Cys Ala Ala Asp Gln<br>595                           600                    605 | 2356 |
| aaa aat cat tac aca tgt cca aac gtt aaa gtt ttc ttc aat gct tcg<br>Lys Asn His Tyr Thr Cys Pro Asn Val Lys Val Phe Phe Asn Ala Ser<br>610                       615                      620 | 2404 |
| atc att tgg ggt gtc att gga ccc caa cgt caa ttc tca cat ggg cag<br>Ile Ile Trp Gly Val Ile Gly Pro Gln Arg Gln Phe Ser His Gly Gln<br>625                           630                    635 | 2452 |
| att tat tat ggg tta ctt ttc ttt ttc atc att ggt gct gtg acc cct<br>Ile Tyr Tyr Gly Leu Leu Phe Phe Phe Ile Ile Gly Ala Val Thr Pro<br>640                       645                    650 | 2500 |
| gtc atc aat tgg tgg atc ttg aaa aaa tgg cca aac tct cca gtc aag<br>Val Ile Asn Trp Trp Ile Leu Lys Lys Trp Pro Asn Ser Pro Val Lys<br>655                  660                    665                    670 | 2548 |
| tat ttg cat tgg cca gtg ttc ttt tct ggg aca ggg tac att cct cca<br>Tyr Leu His Trp Pro Val Phe Phe Ser Gly Thr Gly Tyr Ile Pro Pro<br>675                       680                    685 | 2596 |
| gcc act cca tat aac tat acc tcc tac tgt gct gtg ggt ttg ttc ttt<br>Ala Thr Pro Tyr Asn Tyr Thr Ser Tyr Cys Ala Val Gly Leu Phe Phe<br>690                       695                    700 | 2644 |
| gga tgg tgg att aaa aag aag tgg ttc cac tgg tgg tct aaa tac aac<br>Gly Trp Trp Ile Lys Lys Lys Trp Phe His Trp Trp Ser Lys Tyr Asn<br>705                  710                    715 | 2692 |
| tat tcc ttg tct gcg ggc ttg gat att ggt ttg gca tgg tgc tgc ttg<br>Tyr Ser Leu Ser Ala Gly Leu Asp Ile Gly Leu Ala Trp Cys Cys Leu<br>720                       725                    730 | 2740 |
| atc att ttc ttg tgc ttg agt tta aca aac acc gac ttc cca tcg tgg<br>Ile Ile Phe Leu Cys Leu Ser Leu Thr Asn Thr Asp Phe Pro Ser Trp<br>735                  740                    745                    750 | 2788 |
| tgg gga aac gat gtg atc aac acc act ctc gac act cag gtt gtc acc<br>Trp Gly Asn Asp Val Ile Asn Thr Thr Leu Asp Thr Gln Val Val Thr<br>755                       760                    765 | 2836 |
| aat atc aga cac ata ttg aaa gag gga gag gca ttt ggg cca tct tcc<br>Asn Ile Arg His Ile Leu Lys Glu Gly Glu Ala Phe Gly Pro Ser Ser<br>770                       775                    780 | 2884 |
| tgg taagctgacg aagaaacaca cacacacaca ttattgcttc ctattgtcgt<br>Trp | 2937 |
| gtcttttatg tagatgtaac gtgtttttat aagaatgtaa tttaattatt gtatatatat | 2997 |
| gccaaatatt tttactgcca ttttatattc tttctgccac taaaaatgat aggaggtttt | 3057 |
| gtatactggg tgtgcttgtt ttacacgcgg gctcttttat tattgatttg aacagtctct | 3117 |
| aaggaagtta cgaacttata ggtgagtgct aaaaatgaaa aggggagtga ggttccttct | 3177 |
| tatatccttt ttggcaagta aatgtgtcgt gctttgatat attagaaaga caatccatta | 3237 |
| atagatgaaa tatatattga tgatgaaaaa agtattggtt gttcaaaatg aaagatcaat | 3297 |
| ataaaaattc ggagagaaac gtgatgttta tagagtaaaa aattgagctg ataacttcgc | 3357 |
| aaccaattct gaacaagcat agtttgcaaa tatgaataca tcctagaaaa agtgtaatct | 3417 |
| atgaggaaat atgcaggata ttcatgatct cttagcaaaa tattaaggtt caatcggttt | 3477 |
| tgtgattggt tgcaaaattt atcattcgcg gtgtaagtac accaagaagt tagacaccta | 3537 |
| catgatcttt tttgtttttt caattctttt gatttcctat aaaagttctc ccgttttcct | 3597 |
| ttcctttctt ttctgaaaat gaacaatata gaatatcttt ttttggtgaa atcactgatt | 3657 |
| gcctaacctt cgttcttgaa tttatattct attaatattg ttgtatcatc gctgcttcat | 3717 |
| ttccattcct tctgtttcaa aatcaaatat aaaaagttca aagaatgatc aatagtgaca | 3777 |

```
attttcaagc tcgtgtaaac tgtgaaagta atacaagact ctgcagaata cacatgctga    3837
aaataattaa tgacaaaggt atgttgaaca tgatc                               3872
```

<210> SEQ ID NO 2
<211> LENGTH: 783
<212> TYPE: PRT
<213> ORGANISM: C. albicans

<400> SEQUENCE: 2

```
Met Asp Lys Ile Arg Ala Val Ile Ser Gly Gly Glu Lys Pro Pro Val
 1               5                  10                  15

Asp Thr Asp Asn Asp His Asn Thr Asp Phe Glu Ala Asp Arg Lys Met
            20                  25                  30

Pro Asp Leu Asp Ile Val Val Ser Lys Ser Gln Glu Phe Asp Gln Val
        35                  40                  45

Thr Ser His Leu Val Asn Asp Ile Met Glu Asp Tyr Ala Ala Val
    50                  55                  60

His Val Glu Asp Asp Ser Pro Tyr Pro Glu Val Arg Ala Ala Val Pro
65                  70                  75                  80

Ser Thr Asp Asp Pro Thr Leu Pro Gln Asn Thr Ile Arg Ala Trp Val
                85                  90                  95

Ile Gly Leu Ile Leu Thr Thr Val Gly Cys Gly Met Asn Met Leu Phe
            100                 105                 110

Ser Phe His Ser Pro Ser Phe Ala Ile Thr Thr Phe Val Thr Ser Ile
        115                 120                 125

Leu Ala Trp Pro Ile Gly Asn Phe Trp Ala Trp Ile Val Pro Asp Trp
    130                 135                 140

Lys Ile Phe Gly Ala Ser Leu Ile Pro Gly Pro Phe Asn Val Lys Glu
145                 150                 155                 160

His Thr Ile Ile Thr Ile Met Ala Asn Val Ser Phe Gly Thr Gly Ala
                165                 170                 175

Ala Tyr Ala Thr Asp Ile Leu Leu Ala Gln Asn Met Phe Tyr Lys Ser
            180                 185                 190

Asn Phe Gly Trp Gly Tyr Asn Leu Leu Leu Ile Trp Ser Thr Gln Cys
        195                 200                 205

Ile Gly Phe Ala Phe Gly Ala Val Met Arg Arg Phe Val Val Asp Ser
    210                 215                 220

Pro Gly Ala Ile Trp Pro Leu Asn Leu Val Thr Ala Thr Phe Leu Thr
225                 230                 235                 240

Asn Met His Ile Asn Glu Asn His Thr Ala Asn Gly Trp Lys Ile Ser
                245                 250                 255

Arg Leu Ala Phe Phe Val Ile Val Phe Val Ala Ser Phe Val Trp Tyr
            260                 265                 270

Trp Phe Pro Gly Tyr Ile Phe Gln Ala Leu Ser Tyr Phe Ser Trp Ile
        275                 280                 285

Thr Trp Ile Lys Pro Asn Ile Val Ile Asn Gln Val Phe Gly Ser
    290                 295                 300

Ser Ser Gly Leu Gly Met Ile Pro Asn Asn Ile Ala Leu Asp Trp Asn
305                 310                 315                 320

Gln Ile Ala Gly Tyr Ile Gly Ser Pro Leu Ile Pro Ala Ser Val
                325                 330                 335

Ile Ala Thr Ile Phe Gly Ser Val Leu Ile Phe Trp Ile Val Val
            340                 345                 350
```

```
Pro Ala Ile His Tyr Ser Asn Thr Trp Tyr Ser Gln Tyr Leu Pro Ile
        355                 360                 365

Ser Ser Thr Gly Ser Phe Asp Arg Phe Gln Gln Thr Tyr Asn Val Ser
    370                 375                 380

Lys Ile Ile Asp His Lys Thr Leu Ser Phe Asn Glu Ala Glu Tyr Lys
385                 390                 395                 400

Lys Tyr Phe Pro Leu Phe Leu Ser Thr Thr Phe Ala Ile Ser Tyr Gly
                405                 410                 415

Leu Ser Phe Ala Ser Ile Leu Ala Thr Ile Thr His Thr Ile Cys Phe
            420                 425                 430

His Gly Arg Glu Leu Ile Ala Ser Leu Lys Ala Lys Glu Lys Gln Asp
        435                 440                 445

Val His Asn Arg Leu Met Lys Ala Tyr Lys Pro Val Pro Glu Trp Trp
    450                 455                 460

Tyr Leu Val Val Ser Leu Val Phe Phe Val Met Ser Ile Ala Thr Val
465                 470                 475                 480

Arg Ala Trp Pro Thr Glu Met Pro Val Trp Gly Leu Val Phe Ala Leu
                485                 490                 495

Ile Ile Ala Ile Ile Phe Leu Leu Pro Val Ala Ile Ile Tyr Ala Lys
            500                 505                 510

Thr Asn Asn Ala Val Gly Leu Asn Val Val Thr Glu Phe Ile Val Gly
        515                 520                 525

Tyr Val Leu Gly Gly Arg Pro Leu Cys Met Met Leu Phe Lys Thr Phe
    530                 535                 540

Gly Tyr Ile Thr Asn Asn Gln Ala Val Thr Phe Val Gln Asp Met Lys
545                 550                 555                 560

Leu Gly His Tyr Met Lys Ile Asp Pro Arg Thr Leu Phe Trp Ala Gln
                565                 570                 575

Phe Ala Ala Thr Ile Trp Gly Ser Leu Val Gln Ile Ala Val Leu Glu
            580                 585                 590

Trp Ala Tyr Gly Ala Ile Asp Asn Leu Cys Ala Ala Asp Gln Lys Asn
        595                 600                 605

His Tyr Thr Cys Pro Asn Val Lys Val Phe Phe Asn Ala Ser Ile Ile
    610                 615                 620

Trp Gly Val Ile Gly Pro Gln Arg Gln Phe Ser His Gly Gln Ile Tyr
625                 630                 635                 640

Tyr Gly Leu Leu Phe Phe Phe Ile Ile Gly Ala Val Thr Pro Val Ile
                645                 650                 655

Asn Trp Trp Ile Leu Lys Lys Trp Pro Asn Ser Pro Val Lys Tyr Leu
            660                 665                 670

His Trp Pro Val Phe Phe Ser Gly Thr Gly Tyr Ile Pro Pro Ala Thr
        675                 680                 685

Pro Tyr Asn Tyr Thr Ser Tyr Cys Ala Val Gly Leu Phe Phe Gly Trp
    690                 695                 700

Trp Ile Lys Lys Lys Trp Phe His Trp Ser Lys Tyr Asn Tyr Ser
705                 710                 715                 720

Leu Ser Ala Gly Leu Asp Ile Gly Leu Ala Trp Cys Cys Leu Ile Ile
                725                 730                 735

Phe Leu Cys Leu Ser Leu Thr Asn Thr Asp Phe Pro Ser Trp Trp Gly
            740                 745                 750

Asn Asp Val Ile Asn Thr Thr Leu Asp Thr Gln Val Val Thr Asn Ile
        755                 760                 765

Arg His Ile Leu Lys Glu Gly Glu Ala Phe Gly Pro Ser Ser Trp
```

-continued

```
          770              775              780
```

<210> SEQ ID NO 3
<211> LENGTH: 776
<212> TYPE: PRT
<213> ORGANISM: S. pombe

<400> SEQUENCE: 3

```
Met Ile Gly Ser Ile Asn Glu Ser Pro Ile Glu His Met Asn Asp
 1               5                  10                  15

Ser Pro Ser Thr Lys Glu Lys Ala Asp Ser Val Asp Ile Ser Asp Tyr
                20                  25                  30

Ile Val Ser His Ser Asp Asp Ser Leu Ser Lys Asp Ile Lys Lys Asp
                35                  40                  45

Thr Lys Ser Phe Leu Asp Val Glu His Gly Glu Ile Ser Thr Val Asp
    50                  55                  60

Glu Phe Glu Glu Asp Ser Pro Tyr Pro Glu Val Arg Ala Ala Val Pro
 65                 70                  75                  80

Pro Thr Asp Asp Pro Ser Met Pro Cys Asn Thr Ile Arg Met Trp Thr
                85                  90                  95

Ile Gly Leu Ile Tyr Ser Thr Val Gly Ala Ala Val Asn Met Phe Phe
                100                 105                 110

Ser Leu Arg Asn Pro Thr Val Thr Leu Ser Val Leu Ile Ser Glu Leu
                115                 120                 125

Leu Ala Tyr Pro Ala Leu Gln Ile Trp Asp Leu Ile Phe Pro Asp Arg
    130                 135                 140

Glu Phe Arg Ile Gly Arg Leu Lys Phe Asn Phe Lys Pro Gly Pro Phe
145                 150                 155                 160

Asn Val Lys Glu His Ala Leu Ile Val Val Met Ser Ser Val Ser Phe
                165                 170                 175

Gly Asn Ala Tyr Ser Thr Asp Ile Ile Leu Ala Gln Arg Val His Tyr
                180                 185                 190

Lys Gln Arg Phe Gly Phe Gly Tyr Glu Ile Cys Leu Thr Leu Ala Thr
    195                 200                 205

Gln Leu Ile Gly Tyr Gly Leu Ala Gly Leu Ser Arg Arg Leu Leu Val
    210                 215                 220

Arg Pro Ala Ser Met Leu Trp Pro Val Asn Leu Val Gln Cys Thr Leu
225                 230                 235                 240

Ile Lys Thr Leu His Arg Lys Asp Leu Arg Asn Ala Val Ala Asn Gly
                245                 250                 255

Trp Arg Ile Ser Pro Phe Arg Phe Phe Leu Tyr Val Phe Ile Ala Ser
                260                 265                 270

Phe Ile Trp Asn Trp Ser Pro Ser Tyr Ile Phe Gln Ala Leu Ser Leu
                275                 280                 285

Phe Ala Trp Val Thr Trp Ile Arg Pro Thr Ser Pro Thr Val Asn Gln
    290                 295                 300

Ile Phe Gly Glu Ser Thr Gly Ile Ser Ile Leu Pro Met Thr Phe Asp
305                 310                 315                 320

Trp Asn Gln Ile Ser Ala Tyr Ile Ile Ser Pro Leu Met Ala Pro Ala
                325                 330                 335

Asp Ala Leu Met Asn Ile Leu Leu Gly Val Ile Leu Phe Phe Trp Ile
                340                 345                 350

Val Thr Pro Ala Leu Asn Phe Asn Thr Trp Tyr Gly Asp Tyr Leu
                355                 360                 365
```

-continued

```
Pro Ile Ser Ser Ser Gly Ile Ile Asp His Phe Gly Asn Ser Tyr Asn
370                 375                 380

Val Thr Arg Ile Leu Thr Lys Asp Ala Thr Phe Asp Leu Asp Ala Tyr
385                 390                 395                 400

Gln Asn Tyr Ser Pro Ile Phe Met Ser Thr Thr Tyr Ala Leu Ala Phe
                405                 410                 415

Gly Leu Ser Phe Ala Ser Ile Thr Ser Val Ile Phe His Val Ile Leu
            420                 425                 430

Tyr His Gly Lys Glu Ile Tyr Asp Arg Leu Arg Asp Pro Pro Ala Pro
        435                 440                 445

Asp Ile His Glu Lys Leu Met Lys Ala Tyr Asp Glu Val Pro Phe Tyr
    450                 455                 460

Trp Tyr Leu Ser Val Phe Leu Ala Phe Phe Gly Met Met Met Gly Thr
465                 470                 475                 480

Ile Tyr Gly Trp Lys Thr Glu Thr Pro Trp Trp Val Ile Ile Val Gly
                485                 490                 495

Val Ile Phe Ser Ala Val Trp Phe Ile Pro Ile Gly Ile Val Gln Ala
            500                 505                 510

Ile Thr Asn Ile Gln Leu Gly Leu Asn Val Phe Thr Glu Phe Ile Val
        515                 520                 525

Gly Tyr Met Tyr Pro Gly Arg Pro Leu Ala Met Met Ile Phe Lys Thr
    530                 535                 540

Val Gly Tyr Ile Thr Met Thr Gln Gly Leu Ala Phe Ala Ala Asp Leu
545                 550                 555                 560

Lys Phe Gly His Tyr Met Lys Leu Pro Pro Arg Ile Met Phe Tyr Thr
                565                 570                 575

Gln Met Ile Ala Thr Ile Trp Ser Cys Phe Val Gln Ile Gly Val Leu
            580                 585                 590

Asp Trp Ala Leu Gly Asn Ile Asp Asn Val Cys Gln Ala Asp Gln Pro
        595                 600                 605

Asp Asn Tyr Thr Cys Pro Asn Ala Thr Val Phe Phe Asn Ser Ser Val
    610                 615                 620

Ile Trp Gly Val Ile Gly Pro Lys Arg Met Phe Ser Gly Lys Asn Thr
625                 630                 635                 640

Tyr Thr Gly Leu Gln Tyr Phe Trp Leu Ala Gly Val Leu Gly Thr Ile
                645                 650                 655

Leu Phe Trp Ala Leu Trp Lys Lys Trp Pro Gln Lys Trp Trp Gly Gln
            660                 665                 670

Leu Asn Gly Pro Leu Ile Phe Gly Gly Thr Gly Tyr Ile Pro Pro Ala
        675                 680                 685

Thr Pro Val Asn Tyr Leu Ala Trp Ser Gly Ile Gly Leu Phe Phe Asn
    690                 695                 700

Tyr Tyr Leu Lys Lys Ile Phe Ala Asp Trp Trp Gln Lys Tyr Asn Phe
705                 710                 715                 720

Thr Leu Ser Ala Leu Asp Thr Gly Thr Gln Leu Ser Val Leu Ile Leu
                725                 730                 735

Phe Phe Cys Leu Gln Leu Pro Met Val Asn Phe Pro Asp Trp Trp Gly
            740                 745                 750

Asn Asp Gly Ala Phe Asn Thr Leu Asp Ala Thr Gly Ala Ala Val Arg
        755                 760                 765

Lys Leu Val Asn Glu Ser Ala Arg
    770                 775
```

-continued

```
<210> SEQ ID NO 4
<211> LENGTH: 799
<212> TYPE: PRT
<213> ORGANISM: S. cerevisiae

<400> SEQUENCE: 4
```

| | | | | | | | | | | | | | | | |
|---|---|---|---|---|---|---|---|---|---|---|---|---|---|---|---|
| Met | Ser | Thr | Ile | Tyr | Arg | Glu | Ser | Asp | Ser | Leu | Glu | Ser | Glu | Pro | Ser |
| 1 | | | | 5 | | | | | 10 | | | | | 15 | |
| Pro | Thr | Pro | Thr | Thr | Ile | Pro | Ile | Gln | Ile | Asn | Met | Glu | Glu | Glu | Lys |
| | | | 20 | | | | | 25 | | | | | 30 | | |
| Lys | Asp | Ala | Phe | Val | Lys | Asn | Ile | Asp | Glu | Asp | Val | Asn | Asn | Leu | Thr |
| | | 35 | | | | | 40 | | | | | 45 | | | |
| Ala | Thr | Thr | Asp | Glu | Glu | Asp | Arg | Asp | Pro | Glu | Ser | Gln | Lys | Phe | Asp |
| | 50 | | | | | 55 | | | | | 60 | | | | |
| Arg | His | Ser | Ile | Gln | Glu | Gly | Leu | Val | Trp | Lys | Gly | Asp | Pro | Thr |
| 65 | | | | | 70 | | | | | 75 | | | | | 80 |
| Tyr | Leu | Pro | Asn | Ser | Pro | Tyr | Pro | Glu | Val | Arg | Ser | Ala | Val | Ser | Ile |
| | | | | 85 | | | | | 90 | | | | | 95 | |
| Glu | Asp | Asp | Pro | Thr | Ile | Arg | Leu | Asn | His | Trp | Arg | Thr | Trp | Phe | Leu |
| | | | 100 | | | | | 105 | | | | | 110 | | |
| Thr | Thr | Val | Phe | Val | Val | Val | Phe | Ala | Gly | Val | Asn | Gln | Phe | Phe | Ser |
| | | 115 | | | | | 120 | | | | | 125 | | | |
| Leu | Arg | Tyr | Pro | Ser | Leu | Glu | Ile | Asn | Phe | Leu | Val | Ala | Gln | Val | Val |
| | 130 | | | | | 135 | | | | | 140 | | | | |
| Cys | Tyr | Pro | Ile | Gly | Arg | Ile | Ile | Ala | Leu | Leu | Pro | Asp | Trp | Lys | Cys |
| 145 | | | | | 150 | | | | | 155 | | | | | 160 |
| Ser | Lys | Val | Pro | Phe | Phe | Asp | Leu | Asn | Pro | Gly | Pro | Phe | Thr | Lys | Lys |
| | | | | 165 | | | | | 170 | | | | | 175 | |
| Glu | His | Ala | Val | Val | Thr | Ile | Ala | Val | Ala | Leu | Thr | Ser | Ser | Thr | Ala |
| | | | | 180 | | | | | 185 | | | | | 190 | |
| Tyr | Ala | Met | Tyr | Ile | Leu | Asn | Ala | Gln | Gly | Ser | Phe | Tyr | Asn | Met | Lys |
| | | 195 | | | | | 200 | | | | | 205 | | | |
| Leu | Asn | Val | Gly | Tyr | Gln | Phe | Leu | Leu | Val | Trp | Thr | Ser | Gln | Met | Ile |
| | 210 | | | | | 215 | | | | | 220 | | | | |
| Gly | Tyr | Gly | Ala | Ala | Gly | Leu | Thr | Arg | Arg | Trp | Val | Val | Asn | Pro | Ala |
| 225 | | | | | 230 | | | | | 235 | | | | | 240 |
| Ser | Ser | Ile | Trp | Pro | Gln | Thr | Leu | Ile | Ser | Val | Ser | Leu | Phe | Asp | Ser |
| | | | | 245 | | | | | 250 | | | | | 255 | |
| Leu | His | Ser | Arg | Lys | Val | Glu | Lys | Thr | Val | Ala | Asn | Gly | Trp | Thr | Met |
| | | | 260 | | | | | 265 | | | | | 270 | | |
| Pro | Arg | Tyr | Arg | Phe | Phe | Leu | Ile | Val | Leu | Ile | Gly | Ser | Phe | Ile | Trp |
| | | 275 | | | | | 280 | | | | | 285 | | | |
| Tyr | Trp | Val | Pro | Gly | Phe | Leu | Phe | Thr | Gly | Leu | Ser | Tyr | Phe | Asn | Val |
| | 290 | | | | | 295 | | | | | 300 | | | | |
| Ile | Leu | Trp | Gly | Ser | Lys | Thr | Arg | His | Asn | Phe | Ile | Ala | Asn | Thr | Ile |
| 305 | | | | | 310 | | | | | 315 | | | | | 320 |
| Phe | Gly | Thr | Gln | Ser | Gly | Leu | Gly | Ala | Leu | Pro | Ile | Thr | Phe | Asp | Tyr |
| | | | | 325 | | | | | 330 | | | | | 335 | |
| Thr | Gln | Val | Ser | Gln | Ala | Met | Ser | Gly | Ser | Val | Phe | Ala | Thr | Pro | Phe |
| | | | 340 | | | | | 345 | | | | | 350 | | |
| Tyr | Val | Ser | Ala | Asn | Thr | Tyr | Ala | Ser | Val | Leu | Ile | Phe | Phe | Val | Ile |
| | | 355 | | | | | 360 | | | | | 365 | | | |
| Val | Leu | Pro | Cys | Leu | Tyr | Phe | Thr | Asn | Thr | Trp | Tyr | Ala | Lys | Tyr | Met |
| | 370 | | | | | 375 | | | | | 380 | | | | |

-continued

```
Pro Val Ile Ser Gly Ser Thr Tyr Asp Asn Thr Gln Asn Lys Tyr Asn
385                 390                 395                 400

Val Thr Lys Ile Leu Asn Glu Asp Tyr Ser Ile Asn Leu Glu Lys Tyr
            405                 410                 415

Lys Glu Tyr Ser Pro Val Phe Val Pro Phe Ser Tyr Leu Leu Ser Tyr
                420                 425                 430

Ala Leu Asn Phe Ala Ala Val Ile Ala Val Phe Val His Cys Ile Leu
        435                 440                 445

Thr His Gly Lys Asp Ile Val Ala Lys Phe Lys Asp Arg Lys Asn Gly
    450                 455                 460

Gly Thr Asp Ile His Met Arg Ile Tyr Ser Lys Asn Tyr Lys Asp Cys
465                 470                 475                 480

Pro Asp Trp Trp Tyr Leu Leu Leu Gln Ile Val Met Ile Gly Leu Gly
                485                 490                 495

Phe Val Ala Val Cys Cys Phe Asp Thr Lys Phe Pro Ala Trp Ala Phe
                500                 505                 510

Val Ile Ala Ile Leu Ile Ser Leu Val Asn Phe Ile Pro Gln Gly Ile
            515                 520                 525

Leu Glu Ala Met Thr Asn Gln His Val Gly Leu Asn Ile Ile Thr Glu
530                 535                 540

Leu Leu Cys Gly Tyr Met Leu Pro Leu Arg Pro Met Ala Asn Leu Leu
545                 550                 555                 560

Phe Lys Ile Tyr Gly Phe Ile Val Met Arg Gln Gly Leu Asn Leu Ser
                565                 570                 575

Arg Asp Leu Lys Leu Ala Met Tyr Met Lys Val Ser Pro Arg Leu Ile
                580                 585                 590

Phe Ala Val Gln Ile Tyr Ala Thr Ile Ile Ser Gly Met Val Asn Val
        595                 600                 605

Gly Val Gln Glu Trp Met Met His Asn Ile Asp Gly Leu Cys Thr Thr
610                 615                 620

Asp Gln Pro Asn Gly Phe Thr Cys Ala Asn Gly Arg Thr Val Phe Asn
625                 630                 635                 640

Ala Ser Ile Ile Val Ser Leu Pro Lys Tyr Leu Phe Ser Ser Gly Arg
            645                 650                 655

Ile Tyr Asn Pro Leu Met Trp Phe Phe Leu Ile Gly Leu Leu Phe Pro
                660                 665                 670

Leu Ala Val Tyr Ala Val Gln Trp Lys Phe Pro Lys Phe Lys Phe Ala
        675                 680                 685

Lys His Ile His Thr Pro Val Phe Phe Thr Gly Pro Gly Asn Ile Pro
    690                 695                 700

Pro Ser Thr Pro Tyr Asn Tyr Ser Leu Phe Phe Ala Met Ser Phe Cys
705                 710                 715                 720

Leu Asn Leu Ile Arg Lys Arg Trp Arg Ala Trp Phe Asn Lys Tyr Asn
                725                 730                 735

Phe Val Met Gly Ala Gly Val Glu Ala Gly Val Ala Ile Ser Val Val
                740                 745                 750

Ile Ile Phe Leu Cys Val Gln Tyr Pro Gly Gly Lys Leu Ser Trp Trp
        755                 760                 765

Gly Asn Asn Val Trp Lys Arg Thr Tyr Asp Asn Asp Tyr Lys Lys Phe
    770                 775                 780

Tyr Thr Leu Lys Lys Gly Glu Thr Phe Gly Tyr Asp Lys Trp Trp
785                 790                 795
```

-continued

```
<210> SEQ ID NO 5
<211> LENGTH: 877
<212> TYPE: PRT
<213> ORGANISM: S. cerevisiae

<400> SEQUENCE: 5
```

| | | | | | | | | | | | | | | |
|---|---|---|---|---|---|---|---|---|---|---|---|---|---|---|
| Met | Ser | Glu | Thr | Val | Lys | Asp | Lys | Val | Ile | Ile | Asp | Glu | Lys | Val | Ser |
| 1 | | | | 5 | | | | | 10 | | | | | 15 | |
| Thr | Lys | Gly | Thr | Val | Asp | Tyr | Ala | Glu | Gly | Ala | Glu | Tyr | Ser | Glu | Arg |
| | | | 20 | | | | | 25 | | | | | 30 | | |
| Leu | Ser | Asn | His | Ser | Ser | Asp | Phe | Ser | Gln | Trp | Tyr | Thr | Asp | Glu | Gln |
| | | 35 | | | | | 40 | | | | | 45 | | | |
| Ile | Leu | His | Phe | Met | Lys | Lys | Leu | Gly | Tyr | Glu | Asn | Arg | Thr | Leu | Tyr |
| | 50 | | | | | 55 | | | | | 60 | | | | |
| Asp | Ile | Pro | Glu | Asp | Val | Ala | Tyr | Ile | Leu | Lys | Lys | Met | Pro | Glu | Leu |
| 65 | | | | | 70 | | | | | 75 | | | | | 80 |
| Thr | Leu | Glu | Asp | Ser | Phe | Lys | Ile | Leu | Lys | Asp | Ser | Ile | Ile | Tyr | Phe |
| | | | | 85 | | | | | 90 | | | | | 95 | |
| Lys | Asp | Asp | Glu | Asn | Ile | Pro | His | Asp | Gln | Tyr | Glu | Glu | Trp | Lys | Arg |
| | | | 100 | | | | | 105 | | | | | 110 | | |
| Leu | Val | Asp | Leu | Glu | Asp | Leu | Asp | Ser | Lys | Glu | Gly | Ile | Asp | Glu | Tyr |
| | | 115 | | | | | 120 | | | | | 125 | | | |
| Asp | Ser | Phe | Asp | Ile | Arg | Ala | Phe | Ala | Ser | Ala | Ile | Lys | Phe | His | Ser |
| | 130 | | | | | 135 | | | | | 140 | | | | |
| Pro | Tyr | Gln | Glu | Val | Arg | Ala | Val | Val | Asp | Pro | Glu | Asp | Asp | Pro | Thr |
| 145 | | | | | 150 | | | | | 155 | | | | | 160 |
| Ile | Pro | Val | Glu | Thr | Phe | Arg | Ala | Tyr | Phe | Leu | Ala | Ile | Ile | Trp | Ser |
| | | | | 165 | | | | | 170 | | | | | 175 | |
| Val | Ile | Gly | Ser | Gly | Phe | Asn | Glu | Phe | Phe | Ser | His | Arg | Val | Val | Ser |
| | | | 180 | | | | | 185 | | | | | 190 | | |
| Ile | Ser | Leu | Asn | Thr | Pro | Ile | Ile | Gln | Met | Phe | Leu | Tyr | Ile | Cys | Gly |
| | | 195 | | | | | 200 | | | | | 205 | | | |
| Lys | Ala | Trp | Ala | Lys | Thr | Ile | Pro | Cys | Trp | Thr | Ile | Thr | Ile | Arg | Gly |
| | 210 | | | | | 215 | | | | | 220 | | | | |
| Arg | Lys | Tyr | Gly | Ile | Asn | Ile | Asp | Lys | Pro | Trp | Thr | Gln | Lys | Glu | Gln |
| 225 | | | | | 230 | | | | | 235 | | | | | 240 |
| Met | Phe | Ser | Thr | Leu | Leu | Tyr | Ala | Ile | Cys | Gln | Gly | Ala | Phe | Tyr | Thr |
| | | | | 245 | | | | | 250 | | | | | 255 | |
| His | Tyr | Asn | Ile | Leu | Thr | Gln | Lys | Leu | Phe | Tyr | His | Ser | Ala | Phe | Ser |
| | | | 260 | | | | | 265 | | | | | 270 | | |
| Phe | Gly | Tyr | Gln | Phe | Leu | Leu | Ser | Leu | Ser | Val | Gln | Phe | Ile | Gly | Phe |
| | | 275 | | | | | 280 | | | | | 285 | | | |
| Gly | Phe | Ala | Gly | Ile | Leu | Arg | Lys | Phe | Val | Val | Tyr | Pro | Ala | Arg | Ala |
| | 290 | | | | | 295 | | | | | 300 | | | | |
| Leu | Trp | Pro | Thr | Val | Met | Pro | Thr | Ile | Ala | Ile | Asn | Lys | Ala | Leu | Leu |
| 305 | | | | | 310 | | | | | 315 | | | | | 320 |
| Gly | Lys | Glu | Lys | His | Glu | Ser | Gly | Met | Ser | Arg | Tyr | Lys | Phe | Phe | Phe |
| | | | | 325 | | | | | 330 | | | | | 335 | |
| Leu | Thr | Phe | Phe | Ile | Met | Phe | Ile | Tyr | Asn | Trp | Phe | Pro | Thr | Tyr | Ile |
| | | | 340 | | | | | 345 | | | | | 350 | | |
| Ile | Asn | Ile | Leu | Asn | Thr | Phe | Asn | Trp | Met | Thr | Trp | Ile | Lys | Pro | Ser |
| | | 355 | | | | | 360 | | | | | 365 | | | |
| Asn | Ile | Asn | Leu | Ala | Asn | Ile | Thr | Gly | Gly | Val | Thr | Gly | Leu | Gly | Ile |
| | 370 | | | | | 375 | | | | | 380 | | | | |

```
Asn Pro Ile Ser Ser Phe Asp Trp Asn Val Ile Ser Phe Asn Ser Pro
385                 390                 395                 400

Leu Val Tyr Pro Phe Trp Ser Tyr Leu Thr Gln Tyr Leu Gly Cys Ile
            405                 410                 415

Leu Ala Ala Leu Ile Val Ile Ala Val Tyr Tyr Ser Asn Tyr Met Ser
                420                 425                 430

Cys Gln Tyr Leu Pro Ile Phe Thr Asn Ser Leu Tyr Thr Asn Thr Gly
        435                 440                 445

His Ser Phe Lys Val Thr Glu Val Leu Asp Ser Asp Asn Lys Leu Asp
    450                 455                 460

Val Lys Lys Tyr Gln Ser Tyr Ser Pro Pro Tyr Tyr Ser Ala Gly Asn
465                 470                 475                 480

Leu Val Ser Tyr Gly Ala Phe Ile Cys Ala Tyr Pro Leu Met Ile Thr
                485                 490                 495

Trp Ser Phe Ile Val His Ser Lys Leu Leu Phe Asn Ala Phe Lys Asp
                500                 505                 510

Trp Ala Leu Asn Leu Trp Ala Met Arg Lys Leu Lys Ser Trp Val Thr
            515                 520                 525

Met Phe Lys Ser Asp Tyr Arg Ala Leu Asp Asp Tyr Asp Asp Pro His
530                 535                 540

Ser Asn Ala Met Lys Asn Tyr Lys Glu Val Pro Asp Trp Trp Tyr Phe
545                 550                 555                 560

Ala Ile Leu Ile Gly Ser Leu Val Val Gly Ile Ala Val Val Glu His
                565                 570                 575

Tyr Pro Thr Asn Thr Pro Val Trp Gly Leu Phe Val Cys Leu Gly Phe
                580                 585                 590

Asn Phe Val Phe Leu Ile Pro Thr Thr Ile Leu Gln Ala Thr Thr Gly
            595                 600                 605

Tyr Ser Phe Gly Leu Asn Leu Leu Ile Glu Met Val Met Gly Tyr Ala
            610                 615                 620

Leu Pro Gly Asn Pro Ile Ala Ile Met Ile Leu Lys Ala Phe Gly Tyr
625                 630                 635                 640

Asn Ile Asp Gly Gln Ala Asp Asn Tyr Val Ser Asn Leu Lys Ile Ala
                645                 650                 655

His Tyr Cys Lys Ile Pro Pro Met Ala Leu Phe Arg Gly Gln Cys Val
                660                 665                 670

Ile Val Phe Ile Gln Ile Phe Val Asn Leu Gly Val Leu Asn Trp Gln
            675                 680                 685

Ile Ser Asn Ile Lys Asp Phe Cys Thr Pro His Gln Asn Ala Lys Phe
            690                 695                 700

Thr Cys Pro Asp Ala Val Thr Tyr Tyr Asn Ala Ser Val Val Trp Gly
705                 710                 715                 720

Ala Ile Gly Pro Lys Arg Ile Phe Asn Tyr Ile Tyr Pro Ile Phe Lys
                725                 730                 735

Trp Cys Trp Leu Ile Gly Ala Cys Ile Gly Ile Phe Phe Gly Val Trp
                740                 745                 750

Lys Arg Trp Gly Lys Phe Tyr Pro Arg Tyr Phe Asp Pro Met Leu Phe
            755                 760                 765

Val Gly Gly Met Leu Asn Met Ser Pro Pro Tyr Asn Leu Met Tyr Tyr
            770                 775                 780

Thr Ser Gly Met Ile Val Ser Tyr Ile Ser Gln Tyr Tyr Met Lys Arg
785                 790                 795                 800

His His Leu Asn Leu Trp Glu Lys Tyr Asn Tyr Val Leu Ser Ala Gly
```

-continued

```
                        805                 810                 815
Phe Ser Thr Gly Leu Val Leu Ser Ala Ile Ile Ile Phe Phe Ala Val
                820                 825                 830
Gln Tyr Lys Asp Thr Ala Phe Asn Trp Trp Gly Asn Thr Val Pro Tyr
            835                 840                 845
Ala Gly Ala Asp Gly Val Gly Tyr Pro Leu Lys Asn Ile Thr Asp Thr
        850                 855                 860
Ala Asn Gly Tyr Phe Gly Tyr Ala Pro Gly His Tyr Pro
865                 870                 875
```

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Peptide

<400> SEQUENCE: 6

```
Lys Leu Leu Gly
  1
```

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Peptide

<400> SEQUENCE: 7

```
Lys Leu Gly Leu
  1
```

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Peptide

<400> SEQUENCE: 8

```
Lys Leu Leu Leu Gly
  1               5
```

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: signature
      motif
<220> FEATURE:
<223> OTHER INFORMATION: Xaa at various positions may be any amino acid

<400> SEQUENCE: 9

```
Phe Tyr Xaa Xaa Ile Asn Xaa Gly Ser Leu Ser
  1               5                  10
```

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 10

```
gcatggattg ttcctgactg g                                              21
```

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 11

```
ccaataccaa acaaatgagg c                                              21
```

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: MOD_RES
<222> LOCATION: (4)
<223> OTHER INFORMATION: ethionine

<400> SEQUENCE: 12

Lys Leu Leu Xaa
 1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: MOD_RES
<222> LOCATION: (4)
<223> OTHER INFORMATION: ethionine

<400> SEQUENCE: 13

Lys Leu Ala Xaa
 1

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: MOD_RES
<222> LOCATION: (5)
<223> OTHER INFORMATION: ethionine

<400> SEQUENCE: 14

Lys Leu Leu Leu Xaa
 1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: MOD_RES
<222> LOCATION: (5)
<223> OTHER INFORMATION: ethionine

```
-continued

<400> SEQUENCE: 15

Lys Leu Leu Ala Xaa
 1               5
```